United States Patent
Martin

(10) Patent No.: US 12,235,252 B2
(45) Date of Patent: *Feb. 25, 2025

(54) NETWORKED AIR QUALITY MONITORING

(71) Applicant: INTWINE CONNECT, LLC, Chagrin Falls, OH (US)

(72) Inventor: David Martin, Chagrin Falls, OH (US)

(73) Assignee: INTWINE CONNECT, LLC, Chagrin Falls, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,302

(22) Filed: Jun. 19, 2023

(65) Prior Publication Data

US 2023/0333074 A1 Oct. 19, 2023

Related U.S. Application Data

(63) Continuation of application No. 17/145,480, filed on Jan. 11, 2021, now Pat. No. 11,680,935, which is a
(Continued)

(51) Int. Cl.
*G08B 17/10* (2006.01)
*F24F 11/30* (2018.01)
(Continued)

(52) U.S. Cl.
CPC .......... *G01N 33/0075* (2013.01); *F24F 11/30* (2018.01); *F24F 11/62* (2018.01);
(Continued)

(58) Field of Classification Search
CPC ..... G01N 33/0075; G01N 33/00; F24F 11/30; F24F 11/62; F24F 2110/50; F24F 2110/70; F24F 2110/72
See application file for complete search history.

(56) References Cited

U.S. PATENT DOCUMENTS 5,511,006 A 4/1996 Tachibana et al.
6,288,646 B1 9/2001 Skardon
(Continued)

FOREIGN PATENT DOCUMENTS

EP 0571367 B1 9/1996
WO 2011090763 A2 7/2011

OTHER PUBLICATIONS

International Search Report for PCT Patent Application No. US2013/020779 dated Mar. 15, 2013, 64 pages.
(Continued)

*Primary Examiner* — Toan N Pham
(74) *Attorney, Agent, or Firm* — Amin, Turocy & Watson, LLP

(57) ABSTRACT

Systems, methods, and non-transitory computer-readable media for continuously monitoring residential air quality and providing a trend based analysis regarding various air pollutants are presented herein. The system comprises an air quality monitor located in a residential house, wherein the air quality monitor is configured to measure the level of an air pollutant. The system also includes a server that is communicatively coupled to the air quality monitor, wherein the server is configured to generate a unique environmental fingerprint associated with the residential house.

20 Claims, 15 Drawing Sheets

Related U.S. Application Data continuation of application No. 16/403,861, filed on May 6, 2019, now Pat. No. 10,890,350, which is a continuation of application No. 15/879,552, filed on Jan. 25, 2018, now Pat. No. 10,281,167, which is a continuation of application No. 14/533,305, filed on Nov. 5, 2014, now Pat. No. 9,890,969, which is a continuation of application No. 13/737,102, filed on Jan. 9, 2013, now Pat. No. 8,907,803.

(60) Provisional application No. 61/584,432, filed on Jan. 9, 2012.

(51) Int. Cl.
*F24F 11/62* (2018.01)
*G01N 33/00* (2006.01)
*F24F 110/50* (2018.01)
*F24F 110/70* (2018.01)
*F24F 110/72* (2018.01)

(52) U.S. Cl.
CPC .......... *G01N 33/00* (2013.01); *F24F 2110/50* (2018.01); *F24F 2110/70* (2018.01); *F24F 2110/72* (2018.01)

(56) References Cited

U.S. PATENT DOCUMENTS

| | | | |
|---|---|---|---|
| 6,774,802 B2 | 8/2004 | Bachinski et al. | |
| 7,265,669 B2 | 9/2007 | Call et al. | |
| 7,378,954 B2 | 5/2008 | Wendt | |
| 7,417,553 B2 | 8/2008 | Young | |
| 8,907,803 B2 | 12/2014 | Martin | |
| 9,373,243 B2 | 6/2016 | Martin | |
| 9,890,969 B2 | 2/2018 | Martin | |
| 10,037,685 B2 | 7/2018 | Martin | |
| 10,281,167 B2 | 5/2019 | Martin | |
| 10,825,336 B2 | 11/2020 | Martin | |
| 10,890,350 B2 | 1/2021 | Martin | |
| 11,423,766 B2 | 8/2022 | Martin | |
| 11,649,977 B2* | 5/2023 | He | F24F 11/63 700/276 |
| 11,680,935 B2 | 6/2023 | Martin | |
| 2008/0045156 A1 | 2/2008 | Sakhpara | |
| 2009/0126382 A1 | 5/2009 | Rubino et al. | |
| 2009/0247110 A1 | 10/2009 | Sennett et al. | |
| 2009/0273470 A1 | 11/2009 | Sinkevicius et al. | |
| 2010/0225493 A1 | 9/2010 | Zishaan | |
| 2011/0090763 A1 | 7/2011 | Niemeyer et al. | |
| 2021/0172632 A1* | 6/2021 | Saunders | F24F 11/64 |
| 2022/0404056 A1* | 12/2022 | Bloemer | F24F 11/58 |

OTHER PUBLICATIONS

Microchip TC77 "Thermal Sensor with SPI Interface", Microchip Technology Incorporated, 2002, 22 pages.
Figaro "TGS 2602—for the detection of Air Contaminants", Figaro USA, Inc., Jan. 2005, 2 pages.
Honeywell "HIH-4030/31 Series, Humidity Sensors", Honeywell Sensing and Control, Mar. 2008, 8 pages.
Non-Final Office Action for U.S. Appl. No. 13/737,102 mailed on Mar. 31, 2014, 23 Pages.
Non-Final Office Action for U.S. Appl. No. 14/533,305 mailed on Mar. 9, 2017, 24 Pages.
Non-Final Office Action for U.S. Appl. No. 14/533,305 mailed on Aug. 15, 2017, 9 Pages.
Non-Final Office Action for U.S. Appl. No. 15/879,552 mailed on Jun. 21, 2018, 31 Pages.
Non-Final Office Action for U.S. Appl. No. 16/403,861 mailed on Nov. 1, 2019, 29 Pages.
Final Office Action for U.S. Appl. No. 16/403,861 mailed on Apr. 28, 2020, 10 Pages.
Non-Final Office Action for U.S. Appl. No. 17/145,480 mailed on Jan. 11, 2021, 34 Pages.

* cited by examiner

NETWORKED AIR QUALITY MONITORING

CROSS REFERENCE TO RELATED APPLICATIONS

This application is a Continuation of U.S. patent application Ser. No. 17/145,480, filed Jan. 11, 2021, now U.S. Pat. No. 11,680,935, entitled "NETWORKED AIR QUALITY MONITORING," which is a Continuation of U.S. patent application Ser. No. 16/403,861, filed May 6, 2019, now U.S. Pat. No. 10,890,350, entitled "NETWORKED AIR QUALITY MONITORING," which is a Continuation of U.S. patent application Ser. No. 15/879,552, filed Jan. 25, 2018, now U.S. Pat. No. 10,281,167, entitled "NETWORKED AIR QUALITY MONITORING," which is a Continuation of U.S. patent application Ser. No. 14/533,305, filed Nov. 5, 2014, now U.S. Pat. No. 9,890,969, entitled "NETWORKED AIR QUALITY MONITORING," which is a Continuation of U.S. patent application Ser. No. 13/737,102, filed Jan. 9, 2013, now U.S. Pat. No. 8,907,803, entitled "NETWORKED AIR QUALITY MONITORING" which claims priority to Provisional Application No. 61/584,432 entitled "NETWORKED AIR QUALITY MONITORING" filed Jan. 9, 2012. The entireties of the above noted U.S. Patent Applications and Provisional Applications are hereby incorporated by reference.

TECHNICAL FIELD

The subject matter described and disclosed herein relates to air quality monitoring, and more specifically to remotely monitoring indoor air quality.

BACKGROUND

Air quality has been a popular issue for decades. Air quality is typically in the context of outdoor pollutants such as smog, car exhaust, or smoke. The negative effects of poor outdoor air quality has on an individual's health has been well studied and is commonly known. Now, the focus is moving indoors to the negative effects poor indoor air quality has on a person's health.

Indoor air pollution is one of the world's worst pollution problems. People spend 90% of their time indoors and 65% of their time is in their home. That number is even higher for the patients most vulnerable to poor indoor air quality: bed-ridden patients with chronic disease, the elderly, and infants. These patients suffer from difficulty breathing, wheezing, coughing, and aggravation of chronic respiratory and cardiac conditions.

One such medical condition that is worsened by poor indoor air quality is chronic obstructive pulmonary disease (COPD). COPD is predicted to become the third leading cause of death by 2020. Currently, poor indoor air quality is responsible for 700,000 of the 2.7 million deaths from COPD worldwide. When poor indoor air quality does not cause death, it triggers symptoms in COPD patients.

Poor indoor air quality can also trigger symptoms in asthmatics. The environmental protection agency (EPA) lists secondhand smoke, dust mites, mold, pests, warm-blooded pets, and nitrogen and outside as the most common indoor asthma triggers. Approximately one in ten Americans have been diagnosed with asthma and 70% of them also have allergies. It is estimated that the number of asthmatics will grow to 100 million by 2025.

There have been numerous studies showing an association between indoor air quality and heart disease. In particular, carbon monoxide, nitrogen dioxide, and fine particle mass have been found to trigger episodes in arrhythmia patients. According to another study, particle mass exposure should be considered as a target for treatment of coronary artery disease—the leading cause of death in developed nations.

Still, the study of the health effects from indoor air quality has only just begun. There are links between indoor air exposure and diabetes, obesity, neurodevelopmental disorders, among many others. As the number of people suffering from poor indoor air quality continues to grow, the scientific literature and the awareness of this health issue will grow as well.

Telemedicine has been shown to reduce the cost of healthcare and increase efficiency through better management of chronic diseases by reducing and shortening hospital visits. The providers of telemedicine technology can help hospitals control their costs where it matters most.

In the current administration's healthcare reforms, new legislation will penalize hospitals for readmission. Currently, readmissions are the most costly to the government and the taxpayer taking up nearly 20% of Medicare's $103 billion budget. In fact, one in five patients discharged are readmitted within 30 days. This is widely regarded to be an avoidable problem. However, some patients with chronic diseases will always be coming back.

Due to the chronic and worsening nature of COPD, patients suffering from this disease have some of the highest readmission rates. Consequently, the average annual Medicare expenditure on COPD patients is nearly double that of all covered patients. COPD also has the highest cost of care of all illnesses. Knowing that poor indoor air quality can trigger symptoms in COPD patients, remote and constant monitoring of the indoor air quality in COPD patients' homes can help reduce these costs.

Asthma is responsible for a large number of hospital visits as well. It accounts for 10.5 million visits each year and is the third ranking cause of visits for children under 15. As a result, the direct cost due to asthma in the United States each year is $14.7 billion. While people suffering from asthma know the importance of eliminating triggers from their environment, fewer than 30% know what those triggers are. Constant monitoring of indoor air quality can raise awareness of asthma triggers and prevent millions of hospital visits each year.

SUMMARY

The following presents a simplified summary to provide a basic understanding of some aspects described herein. This summary is not an extensive overview of the disclosed subject matter. It is not intended to identify key or critical elements of the disclosed subject matter, or delineate the scope of the subject disclosure. Its sole purpose is to present some concepts of the disclosed subject matter in a simplified form as a prelude to the more detailed description presented later.

Telemedicine is the future of healthcare and along with it comes telemonitoring. Yet, there is no cost effective method to remotely and continuously monitor indoor air quality. Poor indoor air quality has a negative impact, short-term and long-term, on the health and productivity of those at home, work, and school. It is an increasing issue putting a negative strain on our economy by increasing costs to businesses and healthcare. Telemonitoring of indoor air quality can improve healthcare and control these costs. However, if it is to gain widespread adoption, the technology must be reliable and easy to use.

Currently, there are other commercially available multi-sensor gas detectors. Most detectors used by consumers today are still limited to only carbon monoxide, and unless predefined thresholds are reached to trigger an alarm, homeowners are typically unaware of gas concentration or trends in their homes. For instance, the standards most carbon monoxide detectors adhere to are at levels above the sensitivity levels of patients at risk or with certain respiratory or heart diseases. Another solution available is a home indoor air quality kit. These kits are often expensive, take only one-time readings of the environmental variables, and can be misinterpreted by the homeowner. Environmental watch groups and in-home inspection services also exist. However once again, there are no cost-effective methods for continuously and remotely monitoring conditions when they are not on-site.

In accordance with various embodiments described herein, the disclosed subject matter provides a telemonitoring solution for indoor air quality in residential environments where no other solution exists. The subject matter provides a commercially feasible, efficient, and useful indoor air quality monitor. Generally, commercially feasible gas sensors are not perfectly selective or highly sensitive. Accordingly, the disclosed and described subject matter utilizes algorithms to integrate data from multiple commercially feasible gas sensors in an air quality monitor to develop more accurate data processing and eliminate noise and uncertainty at low levels.

Data integration is used to (1) integrate the data from individual sensors to reach a conclusion about the suitability of the environment at a particular instance in time, (2) detect unfavorable/unhealthy operating conditions, isolate the problem and make an inference about the source, and then alert the user, and (3) use historical information to provide an estimate of future trend. The described data integration capabilities provide methods to not only detect an acute spike in specific hazardous gas concentrations, but also monitor developing trends in concentration. This enables individuals to proactively take necessary action to maintain a healthy living environment before a real risk is present. The subject matter can also send real-time updates or alerts to a homeowner or healthcare provider via e-mail or text message.

In accordance with one or more various embodiments, the subject application describes a networked air quality monitor system, comprising a sensor component that continuously monitors residential air quality to establish data points with respect to disparate pollutants, and a radio module that broadcasts the data points to a server.

In accordance with one or more further embodiments, the subject application describes and discloses a system comprising an air quality monitor located in a residential house, the air quality monitor configured to measure a level of an air pollutant, and a server communicatively coupled to the air quality monitor, the server configured to generate a unique environmental fingerprint associated with a residential house.

In accordance yet one or more additional embodiments, the subject application describes and discloses a method, comprising: receiving data associated with a level of an air pollutant within a residential house, establishing a baseline environmental fingerprint for the residential house as a function of the level of the air pollutant, monitoring subsequent data associated with the level of the air pollutant within the residential house for a deviation from the baseline environmental fingerprint, and in response to the deviation from the baseline environmental fingerprint, transmitting a notification to an air quality monitor situated within the residential house to activate an audio/visual warning indicator.

The following description and the annexed drawings set forth in detail certain illustrative aspects of the disclosed subject matter. These aspects are indicative, however, of but a few of the various ways in which the principles of the subject application can be employed. The disclosed subject matter is intended to include all such aspects and their equivalents. Other advantages and distinctive features of the disclosed subject matter will become apparent from the following detailed description of the various embodiments when considered in conjunction with the drawings.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

Figure 1:
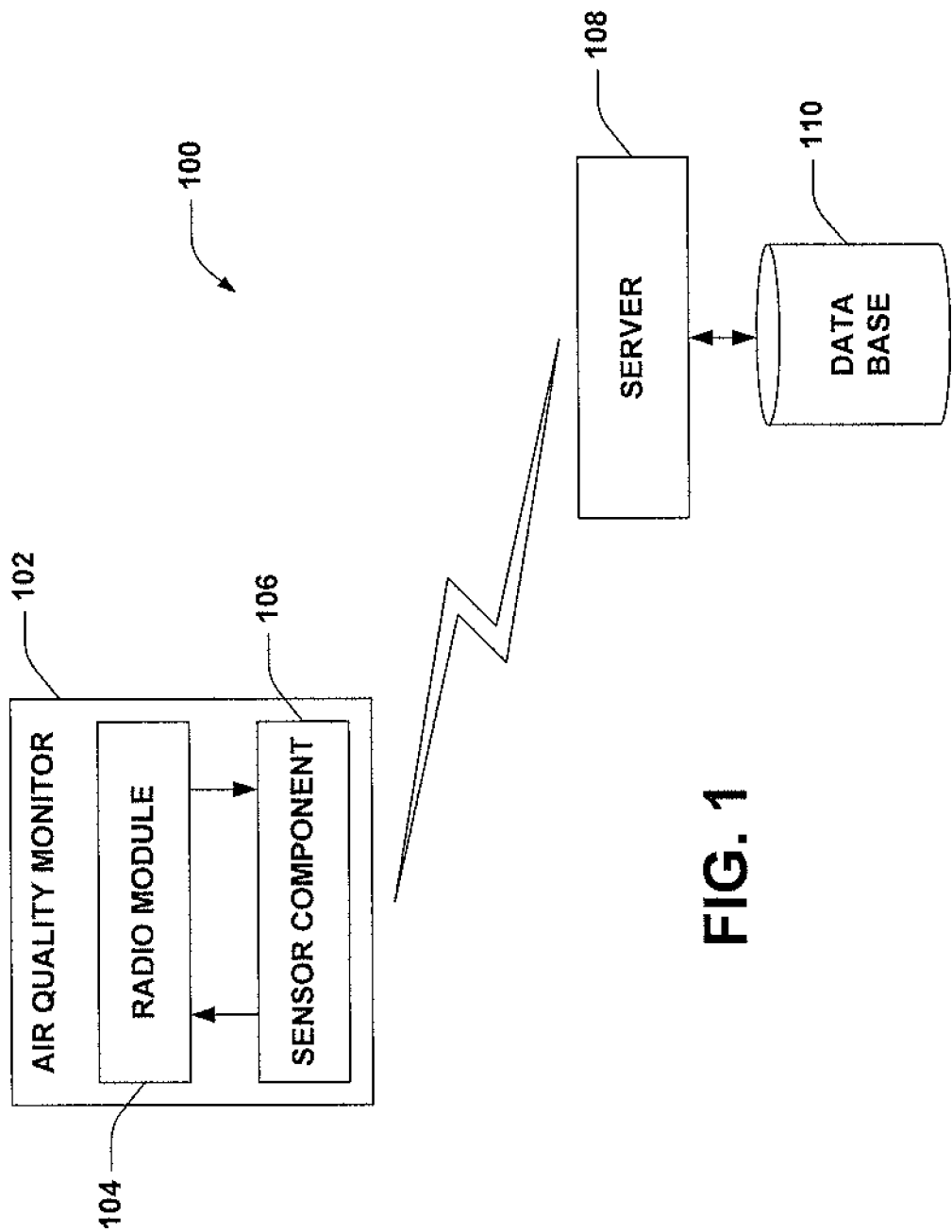
FIG. 1 illustrates a network air quality monitoring system that continuously monitors residential air quality and provides a trend based analysis regarding various air pollutants.

In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment," or "an embodiment," means that a particular feature, structure, or characteristic described in connection with the embodiment is included in at least one embodiment. Thus, the appearances of the phrase "in one embodiment," or "in an embodiment," in various places throughout this specification are not necessarily all referring to the same embodiment. Furthermore, the particular features, structures, or characteristics may be combined in any suitable manner in one or more embodiments.

As utilized herein, terms "component," "system," "interface," and the like are intended to refer to a computer-related entity, hardware, software (e.g., in execution), and/or firmware. For example, a component can be a processor, a process running on a processor, an object, an executable, a program, a storage device, and/or a computer. By way of illustration, an application running on a server and the server can be a component. One or more components can reside within a process, and a component can be localized on one computer and/or distributed between two or more computers.

Further, these components can execute from various computer readable media having various data structures stored thereon. The components can communicate via local and/or remote processes such as in accordance with a signal having one or more data packets (e.g., data from one component interacting with another component in a local system, distributed system, and/or across a network, e.g., the Internet, a local area network, a wide area network, etc. with other systems via the signal).

As another example, a component can be an apparatus with specific functionality provided by mechanical parts operated by electric or electronic circuitry; the electric or electronic circuitry can be operated by a software application or a firmware application executed by one or more processors; the one or more processors can be internal or external to the apparatus and can execute at least a part of the software or firmware application. As yet another example, a component can be an apparatus that provides specific functionality through electronic components without mechanical parts; the electronic components can include one or more processors therein to execute software and/or firmware that confer(s), at least in part, the functionality of the electronic components. In an aspect, a component can emulate an electronic component via a virtual machine, e.g., within a cloud computing system.

The word "exemplary" and/or "demonstrative" is used herein to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

Artificial intelligence based systems, e.g., utilizing explicitly and/or implicitly trained classifiers, can be employed in connection with performing inference and/or probabilistic determinations and/or statistical-based determinations as in accordance with one or more aspects of the disclosed subject matter as described herein. For example, an artificial intelligence system can be used to select appropriate relay stations for secondary transmitter and secondary receivers randomly situated within a cognitive radio network, wherein the secondary receiver and secondary transmitter can base their respective decisions as to which relay station is the most suitable relay station at least in part on links between the relay station and the secondary receiver and the secondary transmitter and the relay station.

As used herein, the term "infer" or "inference" refers generally to the process of reasoning about, or inferring states of, the system, environment, user, and/or intent from a set of observations as captured via events and/or data. Captured data and events can include user data, device data, environment data, data from sensors, sensor data, application data, implicit data, explicit data, etc. Inference can be employed to identify a specific context or action, or can generate a probability distribution over states of interest based on a consideration of data and events, for example.

Inference can also refer to techniques employed for composing higher-level events from a set of events and/or data. Such inference results in the construction of new events or actions from a set of observed events and/or stored event data, whether the events are correlated in close temporal proximity, and whether the events and data come from one or several event and data sources. Various classification schemes and/or systems (e.g., support vector machines, neural networks, expert systems, Bayesian belief networks, fuzzy logic, and data fusion engines) can be employed in connection with performing automatic and/or inferred action in connection with the disclosed subject matter.

In addition, the disclosed subject matter can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, computer-readable carrier, or computer-readable media. For example, computer-readable media can include, but are not limited to, a magnetic storage device, e.g., hard disk; floppy disk; magnetic strip(s); an optical disk (e.g., compact disk (CD), a digital video disc (DVD), a Blu-ray Disc™ (BD)); a smart card; a flash memory device (e.g., card, stick, key drive); and/or a virtual device that emulates a storage device and/or any of the above computer-readable media.

In accordance with an embodiment, the subject application describes and discloses a networked air quality monitor system, comprising: a sensor component that continuously monitors residential air quality to establish data points with respect to disparate pollutants, and a radio module that broadcasts the data points to a server. The server establishes a unique environmental fingerprint using the data points and the disparate pollutants. The unique environmental fingerprint is dependent on characteristics of a residence within which the sensor component is located. The disparate pollutants include air borne particulate matter, volatile organic compounds, nitrogen oxides, carbon monoxide, combustible gases, carbon dioxide, or formaldehyde. The sensor component further comprises a temperature module and a relative humidity module. The sensor component includes a sensor power supply configured to supply power to a particulate sensor, a temperature sensor, a relative humidity sensor, a volatile organic compounds sensor, a nitrogen oxides sensor, a carbon monoxide sensor, a combustible gas sensor, a carbon dioxide sensor, or a formaldehyde sensor. The sensor power supply is configured to pre-heat the volatile organic compound sensor, the nitrogen oxides sensor, the combustible gas sensor, the carbon dioxide sensor, or the formaldehyde sensor. The particulate sensor further comprises an audio/visual indicator configured to alert a user regarding an elevated level of one or more of the disparate pollutants.

In accordance with yet further embodiments, the subject application describes and discloses a system, comprising: an air quality monitor located in a residential house, the air quality monitor is configured to measure a level of an air pollutant, the air quality monitor is communicatively coupled to a server configured to generate a unique environmental fingerprint associated with the residential house. It should be noted in relation to the usage herein of the term residential house, that a residential house can include multi-family dwellings, apartment buildings, mobile homes, recreational vehicles, houseboats, motor homes, ships (e.g., passenger ships, cargo ships, bulk carriers, container ships, . . . ), airplanes, buses, hotels, schools, school rooms, class rooms, sports stadia, concert halls, movie theaters, and the like.

The server continuously monitors the level of the air pollutant based on data broadcast by the air quality monitor. The server further compares the level of the air pollutant against the unique environmental fingerprint established by the server and associated with the residential house. In response to an upward deviation between the level of the air pollutant and the unique environmental fingerprint associated with the residential house, the server broadcasts a notification to a user to take remedial action to abate the upward deviation of the air pollutant. The server broadcasts the notification to the user through use of a short message service (SMS), a multimedia messaging service (MMS), a paging service, an e-mail, or telephonically. Further, in response to an upward deviation between the level of the air pollutant and the unique environmental fingerprint associated with the residential house, the server broadcasts a notification to the air quality monitor to activate an audio/visual warning indicator. The server compares the level of the air pollutant against a threshold deviation value that is a function of the unique environmental fingerprint and in response to the level of the air pollutant exceeding the threshold deviation, the server broadcasts a notification to the air quality monitor to activate an audio/visual warning indicator. The server compares the level of the air pollutant against a threshold deviation value that is a function of the unique environmental fingerprint and in response to the level of the air pollutant exceeding the threshold deviation, the server broadcasts a notification to a user to take remedial action to take action to evacuate the air pollutant.

Additionally, the air quality monitor includes a radio module and a sensor component. The radio module is configured to wirelessly communicate with a wireless access point located in the residential house or the server that is located remotely. The radio module is also configured to wirelessly communicate with a second air quality monitor located in a second location within the residential house. The radio module can also be configured to wireless communicate with an air quality monitor located outside the residential house.

The sensor component can include a group of components that include or comprise one of a power supply, a particulate sensor, a temperature sensor, a relative humidity sensor, a volatile organic compound sensor, a nitrogen oxides sensor, a carbon monoxide sensor, a combustible gas sensor, a carbon dioxide sensor, and/or a formaldehyde sensor. The power supply can be configured to provide power to heaters associated with the volatile organic compound sensor, the nitrogen oxides sensor, the combustible gas sensor, the carbon dioxide sensor, or the formaldehyde sensor.

The particulate sensor can further include a power regulator and one or more audio/visual indicators, wherein the one or more audio/visual indicators are configured to alert a user regarding an elevated level of an air pollutant and the power regulator modulates power received from the power supply. In response to receipt of input from the particulate sensor, the temperature sensor, the relative humidity sensor, the volatile organic compound sensor, the nitrogen oxides sensor, the carbon monoxide sensor, the combustible gas sensor, the carbon dioxide sensor, and/or a formaldehyde sensor, the server can synthesize the input to generate the unique environmental fingerprint associated with the residential house.

The air quality monitor can filter conflicting readings associated with two or more of the particulate sensor, the volatile organic compound sensor, the nitrogen oxides sensor, the carbon monoxide sensor, the combustible gas sensor, the carbon dioxide sensor, or a formaldehyde sensor. Further, the server can also filter conflicting readings that are associated with detection of the air pollutant by two or more of the particulate sensor, the volatile organic compound sensor, the nitrogen oxides sensor, the carbon monoxide sensor, the combustible gas sensor, the carbon dioxide sensor, or a formaldehyde sensor.

The server utilizes the level of the air pollutant received from the air quality monitor and a level of the air pollutant previously persisted to a database to generate a graph of a rise of the air pollutant over time or a graph of a fall of the air pollutant over time. The server can utilize an artificial intelligence component, the level of the air pollutant received from the air quality monitor, and the level of the air pollutant previously persisted to the database to ascertain or determine a future rise of the air pollutant or a future fall of the air pollutant. In response to the artificial intelligence component predicting the future rise of the air pollutant, the server broadcasts a notification to a user to take remedial action to abate the future rise of the air pollutant through use of a short message service (SMS), a multimedia messaging service (MMS), a paging service, an e-mail, or telephonically. In response to the artificial intelligence component predicting the future rise of the air pollutant, the server can also transmit a signal to the air quality monitor to activate an audio/visual warning indicator.

Additionally, in accordance with yet further embodiments, the subject application describes and discloses a method, comprising: receiving data associated with a level of an air pollutant within a residential house; establishing a baseline environmental fingerprint for the residential house as a function of the level of the air pollutant; monitoring subsequent data associated with the level of the air pollutant within the residential house for a deviation from the baseline environmental fingerprint; and in response to the deviation from the baseline environmental fingerprint, transmitting a notification to an air quality monitor situated within the residential house to activate an audio/visual warning indicator.

It should be noted that the systems and methods described and detailed herein can also be communicatively coupled with other health information systems and/or other in-home sensing modalities, such as pulse-ox monitors, motion sensors, and the like.

It should also be noted that while the subject application has been explicated herein in terms of an air quality monitor communicatively coupled to a server (see e.g., FIG. 1), the subject application can also include the use of a plug computer (e.g., a small form factor server for use in a home or office typically enclosed in an AC power plug or AC adapter). The plug computer can provide store-process-forward facilities wherein sensor inputs that can be continuously and/or periodically received from one or more sensors associated with an air quality monitor located in a residential house can be stored on a persistence medium associated with the plug computer. Sensor inputs can also be processed by the plug computer and/or sent to a server for further processing. The plug computer can be connected to a cellular network router via wired or wireless Ethernet, for example. Advantages of using a plug computer, for example, are that it allows local storage to guarantee that no sensor data is lost due to disruptions to broadband connectivity, enables sensor inputs to be stored locally and/or compressed/shaped so as to reduce the amount of data that needs to be transmitted (e.g., to a remote server), enables data transmissions of aggregated sensor inputs to be performed when the cost associated with transmitting data is reduced (e.g., at night) or when the network is underutilized, etc. Further, use of a plug computer enables researchers and healthcare providers to correlate rises and falls in pollutant levels to patient health as well as allowing remote monitoring of patients and their environments within the patient's house. Additionally, the plug computer can also allow remote actuation of various devices based on input received from the air quality monitor and its associated sensors. For instance, a plug computer can be used to actuate ventilators, dehumidifiers, and the like to improve the air quality within the residential house.

Additionally it should be noted; the subject application can be integrated or associated with a patient data system that can enable a healthcare provider the ability to identify dangerous trends and triggers when correlating patient data and/or air quality data. Further as will be observed, the subject application can employ software that fuses patient data with air quality data to generate alerts to enable a home care provider to take appropriate actions.

Furthermore, the subject application can be utilized to monitor the buildup of mold spores with residential homes. This facility can be particularly beneficial where a residential house has been subject to flooding and/or flood damage and the flooding and/or flood damage has subsequently been remediated. Prior to the homeowners being allowed to reenter and reestablish residence in the house, the methods and systems described and disclosed herein can be employed to verify and ensure that mold as a consequence of the flooding and/or flood damage is not a health hazard within the monitored residential house.

Turning now to the Figures. FIG. 1 illustrates a network air quality monitoring system 100 that continuously monitors residential air quality and provides a trend based analysis regarding various air pollutants, such as airborne particulate matter, volatile organic compounds, nitrogen oxides, carbon monoxide, combustible gases, carbon dioxide, and/or formaldehyde. Additionally, network air quality monitoring system 100 can provide feedback to a homeowner regarding elevated levels of these air pollutants. Such feedback can be useful when a homeowner or a member of his/her family suffers from a respiratory ailment such as asthma, chronic obstructive pulmonary disorder (COPD) and the like. As illustrated in FIG. 1 network air quality monitoring system 100 can include air quality monitor 102 that can be in communication with server 108 and its associated database or data store 110. Typically, air quality monitor 102 can be located in a residential home. Generally, air quality monitor 102 can be positioned in an area where a person suffering from a respiratory ailment such as asthma or chronic obstructive pulmonary disorder spends most of their time within the residential house. For instance, air quality monitor 102 can be located in the common areas of the house, such as the living room, dining room, kitchen, study, and the like.

Air quality monitor 102 can include a radio module 104 and a sensor component 106. Radio module 104 can provide wireless communication between air quality monitor 102 and server 108 and its associated database or data store 110. Radio module 104 can also provide wireless communication between air quality monitor 102 and other disparate wireless devices that can be extant within the residential house, such as access points, access terminals, wired and/or wireless routers, cell phones, smart phones, laptops, handheld communication devices, handheld computing devices, satellite radios, global positioning systems, personal digital assistants, and/or any other suitable device for communicating over a wireless communication system or interacting with a wired communication network, such as the Internet. In order to provide this facility, radio module 104 can include multiple antenna groups, and can include a transmitter chain and a receiver chain, each of which in turn can comprise a plurality of components associated with a signal transmission and reception (e.g., processors, modulators, multiplexers, demodulators, demultiplexers, antennas, etc.), as will be appreciated by those reasonably skilled in the art.

Radio module 104, as stated above, can communicate with server 108, one or more mobile device, end user equipment, or access terminal, such as cell phones or a smart phones; however it is to be appreciated that radio module 104 can communicate with substantially any number of mobile devices, access terminals, and/or user equipment. As mentioned above, such mobile devices, user equipment, or access terminals can include handheld communication devices, satellite radios, other wired and/or wireless communication infrastructure (e.g., access points), and the like for wirelessly communicating over a wireless cellular network or interacting with a wired communication network. Generally, where such end user equipment and/or server 108, for instance, is communicating with radio module 104 included in air quality monitor 102, the user equipment and/or server 108 will communicate by way of one or more antennas associated with radio module 104. Thus for instance, where server 108 is in communication with radio module 104 included in air quality monitor 102, transmission of information from radio module 104 to server 108 can be performed over a forward link and information received by radio module 104 from server 108 can be performed over a reverse link. In a frequency division duplex (FDD) system, the forward link can utilize a different frequency band than that used by the reverse link. Further, in a time division duplex (TDD) system the forward link and the reverse link can employ a common frequency.

Each group of antennas associated with radio module 104 and/or the area into which each group of antennas is designated to communicate can be referred as a sector. For example, antenna groups can be designed to communicate to access terminals or user equipment in a sector wherein antennas transmitting over forward links can utilize beamforming to improve signal-to-noise ratio of the forward links.

Air quality module 102 can also include sensor module 106 that can include sensors for detecting the presence of airborne particulate matter such as mold spores, animal hair and dander, and dust, volatile organic compounds typically released from building materials utilized in home construction, such as formaldehyde, and the like, nitrogen oxides, carbon monoxide, combustible gases, such as methane, ethane, etc., carbon dioxide, cigarette smoke, chemicals from cleaning products, gases seeping through house foundations, and the like. Additionally, sensor module 106 can also include temperature sensors and/or relative humidity sensors that can detect rises and falls in temperature and/or relative humidity within the residential house within which air quality monitor 102 is located.

In accordance with an additional and/or alternative embodiment, air quality monitor 102 can also include a store-process-forward aspect wherein sensor inputs received from sensor module 106 can be stored on a persistence medium included and/or associated (e.g., in the cloud) with air quality monitor 102. Sensor inputs can thereafter be processed by one or more processors included and/or associated with air quality monitor 102 and/or forwarded to server 108 for further processing and/or post-processing. The beneficial advantages of including the store-process-forward aspect within air quality monitor 102 are, for instance, that such facilities permit local storage of sensor data thereby ensuring that no sensor data or processed data is lost due to disruptions to broadband connectivity. Further advantages can also include the ability to compress or shape the locally stored sensor data and/or processed data to reduce the amount of data the needs to be transmitted to server 108 and/or to enable data transmissions of aggregated sensor inputs and/or processed data when the costs associated with data transmission are reduced. Additionally, the store-process-forward aspect can enable researchers and healthcare providers the ability to correlate rises and falls in pollutant levels to patient health as well as enabling remote monitoring of patients within their living environments. Moreover, the store-process-forward facility can allow for the remote activation or automatic activation of various devices based on input received by air quality monitor 102 from its associated sensors and processors. For example, air quality monitor 102 can be used to automatically actuate air purifiers, ventilators, dehumidifiers, and the like when it is noted by processes executing on processors include with air quality monitor 102 that air quality within a habitable space has deteriorated beyond acceptable boundaries.

As stated above, air quality monitor 102 and server 108 can be communicatively coupled with one another through a wireless forward link and/or reverse link. During communication between the air quality monitor 102 and server 108, air quality monitor 102 can broadcast data points associated with detected pollutant levels within the residential house. Air quality monitor 102 can continually monitor the environment within the residential house for the presence of air pollutants and can thereafter dispatch the levels or detected levels of air pollutants to server 108.

Server 108 on receipt of the detected pollution levels from air quality monitor 102 can persist the received information to database or data store 110 and thereafter can analyze the received information to determine whether any trends can be detected regarding whether levels of specific pollutants are rising or falling and/or whether there has been any rise or fall in relative humidity and/or temperature within the residential house. It should be noted that server 108 in conjunction with air quality monitor 102 continuously and constantly monitors the level of air pollutants and/or temperature and/or relative humidity within the residential house. Further, server 108, based at least in part upon the received information regarding the pollutant levels, temperature and/or relative humidity levels within the residential house, can generate or construct an environmental fingerprint associated with the residential house. This environmental fingerprint, because each house is designed, configured, and furnished differently, is generally unique and distinct; generally no two houses will have an identical environmental fingerprint. Typically, server 108 generates or constructs the environmental fingerprint associated with the residential house when the first results (initial results, initializing results) are sent from air quality monitor 102 to server 108. This initial environmental fingerprint can provide a baseline from which the server 108 can determine whether or not air pollutants, temperature, and/or relative humidity within the house are rising or falling. Where server 108 detects that one or more of the detected air pollutants, temperature, and/or relative humidity is rising (or falling) and/or has exceeded (or has fallen below) a pre-established or predetermined threshold, server 108 can dispatch notifications to the homeowner, via e-mail, telephonically, using a short message service (SMS), a multi message service (MMS), a paging service, or the like, to inform him/her that actions need to be taken to abate the rise (or fall) in the pollutant, temperature, and/or relative humidity levels. Additionally and/or alternatively in this context, server 108 can broadcast a message or signal to air quality monitor 102 indicating that air quality monitor 102 should activate one or more audio/visual warning indicators that can be associated with sensor component 106.

In the context of building, constructing, establishing and/or utilizing an environmental fingerprint unique to the residential house within which the air quality monitor 102 has been situated, it should be noted that the environmental fingerprint can evolve over time. For instance, the environmental fingerprint can be updated periodically or continuously with context-sensitive safety thresholds (e.g., for a given geography or time of the year); with trend-adjusted targets; and/or with emerging externalities (e.g., weather, pollution, and outside air quality warnings). Additionally, the environmental fingerprint can be updated (dynamically, continuously, periodically, . . . ) utilizing external sources, such as health information systems where mutually agreed-upon targets can be communicated to and acted upon by the server 108 and/or air quality monitor 102.

Typical audio/visual warning indicators that can be activated based on the message or signal received/dispatched from server 108 can include alarms, such as horns, buzzers, etc. and flashing light emitting diodes (LEDs). These audio/visual warning indicators and/or dispatched notifications provide a method of informing the homeowner, and/or any individuals within the residential house suffering from respiratory ailments, that the air quality has deteriorated or is deteriorating to deleterious levels because of the rising levels of air pollutants and/or humidity and/or temperatures within the house and that action needs to be taken to either abate the air pollutants (e.g., by ventilating the house) or by moving to a safe zone within the house where there are devices such as air conditioners, heaters, coolers, air filters, or air purifiers that can better control air quality.

In the context of air quality monitor 102, air quality monitor 102 in addition to being located in common areas of the residential house can also be located in other less frequented areas of the residential house. Additionally and/or alternatively, multiple air quality monitors can be co-located within the residential house. For instance, a first air quality monitor 102 can be located in the common areas of the residential house and a second air quality monitor (e.g., air quality monitor 102) can be located in one or more less frequented areas of the residential house. Further, air quality monitor 102 can also be located externally to the residential house. Thus for example, a first air quality monitor 102 can be located in the common area of the residential house and a second air quality monitor 102 can be located outside the residential house. Where there are two or more air quality monitors dispersed within the residential house and/or externally to the residential house, such a quality monitors can effectuate communication directly with server 108 and/or can effectuate communication with server 108 by nominating one of the two or more air quality monitors to facilitate communication with server 108.

In context of air quality monitor 102 and/or server 108, it should be noted that, while not depicted for reasons of brevity, both air quality monitor 102 and/or server 108 can also include one or more processors to facilitate operation of computer executable components and instructions by the air quality monitor 102 and/or server 108, and one or more memories for storing the computer executable components and instructions that can be employed to facilitate and/or effectuate the various aspects described herein.

Further, in regard to air quality monitor 102 and/or server 108, when either the air quality monitor 102 and/or server 108 detects, depending on the pollutant at issue, that the air quality within the residential house exceeds or falls below a minimum or maximum threshold the server 108 and/or the air quality monitor 102 can actuate an extreme ventilation function wherein a ventilator can be utilized to evacuate the noxious pollutant from the residential house or vent external air into the residential house. In this aspect it should be noted that one or more sensors can be associated with sensor component 106 that are capable of measuring the replacement rate of air or the airflow within the residential house.

In regard to the capabilities and/or functionalities of air quality monitor 102, it should be noted that in certain circumstances air quality monitor 102 can operate independently from and/or in conjunction with input received from server 108. For instance, air quality monitor 102 can automatically (e.g., without input from server 108) activate air purifiers, ventilators, dehumidifiers, air conditioners, etc. located within a habitable space when it is determined that air quality has deteriorated beyond acceptable maximum or minimum levels. This facility can be actuated with or without the necessity of notifications being dispatched by sever 108. Similarly, air quality monitor 102, as a function of input received from server 108, can actuate one or more air purifiers, ventilators, air conditioners, and the like when server 108 identifies that air quality within a confined habitable space has crossed the one or more thresholds or set points that can define an acceptable air quality. Once again, the automatic activation of air purifiers, ventilator, mass air evacuators, and the like can be accomplished with or without the requirement for broadcast notifications.

Figure 2:
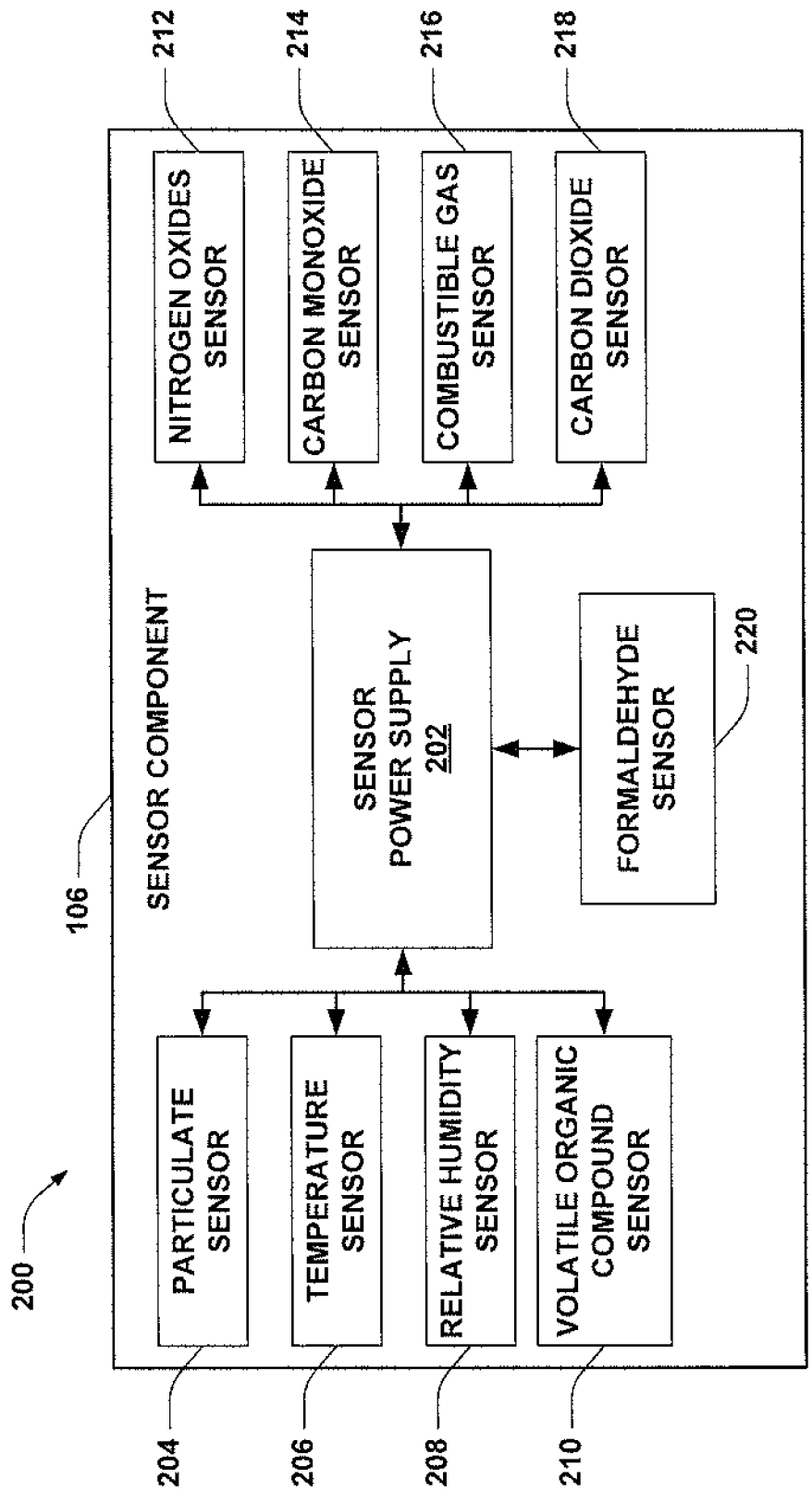
FIG. 2 provides a more detailed depiction of a sensor component in accordance with an aspect of the subject application.

Turning now to FIG. 2 that provides a more detailed depiction of sensor component 106. As illustrated sensor component 106 can include particulate sensor 204, temperature sensor 206, relative humidity sensor 208, volatile organic compound sensor 210, nitrogen oxides sensor 212, carbon monoxide sensor 214, combustible gas sensor 216, carbon dioxide sensor 218, and/or formaldehyde sensor 220. The noted sensors can each be coupled to a sensor power supply 202 that can be configured to satisfy the power requirements for each of the sensors. As will be noted, the power requirements for each of the enumerated sensors can differ markedly, and as such sensor power supply 202 can satisfy and adjust the supply of power to meet the disparate power needs of each of the above noted sensors.

Typically, sensor power supply 202 is configured to provide power to the heaters that can be associated with each of the volatile organic compound sensor 210, nitrogen oxides sensor 212, combustible gas sensor 216, carbon dioxide sensor 216, or formaldehyde sensor 220. Further, sensor power supply 202 can also be configured to regulate the supplied power to each of the included sensors (e.g., particulate sensor 204, temperature sensor 206, relative humidity sensor 208, volatile organic compound sensor 210, nitrogen oxides sensor 212, carbon monoxide sensor 214, combustible gas sensor 216, carbon dioxide sensor 218, and formaldehyde sensor 220) as well as regulate power supplied to one or more audio/visual indicators, wherein the one or more audio/visual indicators are configured to alert a residential homeowner of the elevated levels of air pollutants extant within the residential house.

Particulate sensor 204 in accordance with one or more embodiments can be a laser particle counter that allows monitoring of indoor air quality and detection of small (e.g., bacteria, mold, etc.) and large (pollen, etc.) particulate matter. Particulate sensor 204 can be configured to count individual particles and provide an immediate response to changing environments. Particulate sensor 204 can thereby allow server 108 to ascertain whether or not the indoor ambient environment within the residential house is clean and/or is free of airborne particulate matter.

Temperature sensor 206 in accordance with one or more various embodiments can be a serially accessible digital temperature sensor, wherein temperature data is converted from an internal thermal sensing element and made available at any time as, for example, a 13-bit two's compliment digital word. In accordance with an illustrative embodiment, communication with temperature sensor 206 can be accomplished via a SPI and MICROWIRE compatible interface. Temperature sensor 206 can have a 12-bit plus sign temperature resolution of 0.0625° C. per Least Significant Bit. Generally, temperature sensor 206 can offer a temperature accuracy of ±1.0° C. (max.) over the temperature range from +25° C. to +65° C. When operating, temperature sensor 206 can consume only 250 µA (typ.). Further, temperature sensor 206 can include a configuration register that can be used to activate a low power Shutdown mode, which can have a current consumption of only 0.1 µA (typ).

In accordance with one or more embodiments, relative humidity sensor 208 can be a covered integrated circuit humidity sensor. In one or more further embodiments, relative humidity sensor 208 can be a covered, condensation-resistant, integrated circuit humidity sensor with a hydrophobic filter allowing it to be used in condensing environments including industrial, medical, and commercial applications. Relative humidity sensor 208 can use a laser trimmed, thermoset polymer capacitive sensing element with on-chip integrated signal conditioning. The sensing element's multilayer construction provides excellent resistance to most application hazards such as condensation, dust, dirt, oils, and, common environmental chemicals. Generally, the typical current draw of relative humidity sensor 208 can be in the range of about 200 µA.

Volatile organic compound sensor 210 in accordance with one or more various embodiments can be a sensing element comprised of a metal oxide semiconductor layer formed on an alumina substrate of a sensing chip together with an integrated heater. In the presence of detectable gas, sensor conductivity increases depending on gas concentration in the air. A simple electrical circuit can convert the change in conductivity to an output signal which corresponds to the gas concentration. Generally, volatile organic compound sensor 210 has high sensitivity to low concentrations of odorous gases, such as ammonia and hydrogen sulfide generated from waste materials typically found in an office and home environments. Volatile organic compound sensor 210 can also have high sensitivity to low concentrations of volatile organic compounds such as toluene emitted from wood finishing and construction products.

Nitrogen oxides sensor 212 in accordance with one or more embodiments can be a sensor that detects very low concentrations of nitrogen oxides, in the range from 0.5 ppm to 10 ppm (and typically less than 0.5 ppm to in excess of 10 ppm), for example. Where a larger dynamic detection range is required (e.g., in the range from at least 5 ppm to 100 ppm) nitrogen oxides sensor 212 can be augmented with a heater. Generally, nitrogen oxides sensor 212 can be operational within an environmental temperature range from 20° C. to 50° C. (and typically from less than or equal to 20° C. to in excess of 50° C.) and an environmental humidity range from 0 to 90% relative humidity, non-condensing.

Carbon monoxide sensor 214, like volatile organic compound sensor 210, can be a sensing element comprised of a metal oxide semiconductor layer formed on an alumina substrate of a sensing chip together with an integrated heater, wherein in the presence of a detectable gas, sensor conductivity can increase depending on gas concentration in the air. A simple electrical circuit can convert the change in conductivity to an output signal that corresponds to the gas concentration.

Combustible gas sensor 216 can be similar to nitrogen oxides sensor 212, and can be a sensor that detects very low concentrations of combustible gases, typically in the range from 0.1 ppm to 100 ppm or in the range of 0.5 ppm to 10 ppm, for instance. Like nitrogen oxides sensor 212, combustible gas sensor 216 can be augmented with a heating aspect; this can be particularly useful where a larger dynamic detection range is required.

Carbon dioxide sensor 218 can be a sensor that is similarly configured to nitrogen oxides sensor 212 and combustible gas sensor 216. Like nitrogen oxides sensor 212 and combustible gas sensor 216, carbon dioxide sensor 218 can be a sensor that detects very low concentrations of carbon dioxide, in the range from 0.1 ppm to 250 ppm or from 0.5 ppm to 10 ppm. Further, where a larger dynamic detection range is necessary (e.g., in the range from 5 ppm to 100 ppm) carbon dioxide sensor 218 can be operational with an associated heater. As noted above, carbon dioxide sensor 108, like nitrogen oxide sensor 212, can be operational within an environmental temperature range from 20° C. to 50° C. (and typically from less than or equal to 20° C. to in excess of 50° C.) and an environmental humidity range from 0 to 90% relative humidity, non-condensing.

Formaldehyde sensor 220 in accordance with various embodiments can be a sensor similarly configured to volatile organic compound sensor 210 and/or carbon monoxide sensor 214. Like volatile organic compound sensor 210 and/or carbon monoxide sensor 214, formaldehyde sensor 220 can be a sensing element comprised of a metal oxide semiconductor layer formed on an alumina substrate of a sensing chip together with an integrated heater. In the presence of detectable gas, sensor conductivity can increase depending on gas concentrations in the air. A simple electrical circuit can convert the change in conductivity to an output signal that can correspond to the gas concentration. Generally, formaldehyde sensor 220 can have high sensitivity to low concentrations of gases, such as ammonia, hydrogen sulfide, and volatile organic compounds such as toluene typically emitted from wood finishing and construction products.

It should be noted, and as will be appreciated by those of ordinary skill in this field of endeavor, that particulate sensor 204, temperature sensor 206, relative humidity sensor 208, volatile organic compound sensor 210, nitrogen oxide sensor 212, carbon monoxide sensor 214, combustible gas sensor 216, carbon dioxide sensor 218, and/or formaldehyde sensor 220 can, as described above, be separate/distinct sensors included in sensor component 106, or can be a combination sensor component, wherein disparate sensing capabilities can be included on one or more individual or individuated sensors. For instance, the functionalities provided by carbon monoxide sensor 214 and carbon dioxide sensor 218 can be combined into one sensor component. Further, the functionalities provided by nitrogen oxides sensor 212, combustible gas sensor 216, and/or carbon dioxide sensor 218 can be combined into a single sensor, for example. Moreover, the capabilities of all the aforementioned sensor components (e.g., particulate sensor 204, temperature sensor 206, relative humidity sensor 208, volatile organic compound sensor 210, nitrogen oxide sensor 212, carbon monoxide sensor 214, combustible gas sensor 216, carbon dioxide sensor 218, and/or formaldehyde sensor 220) can, if necessary, be provided on a single component, for instance.

As will have been noted by those ordinarily skilled in this field of endeavor, there can be instances where two or more sensors included in sensor component 106 can detect the presence of airborne particulate matter and/or harmful gases (e.g., volatile organic compounds, nitrogen oxides, carbon monoxide, combustible gases, carbon dioxide, and/or formaldehyde). In order to ensure that false or conflicting readings are not dispatched for analysis to server 108, sensor component 106 can include a filtering aspect that filters out conflicting readings associated with two or more of the constituent sensors included in sensor component 106. Thus for instance, the filtering aspect can filter out conflicting readings from two or more of particulate sensor 204, volatile organic compound sensor 210, nitrogen oxide sensor 212, carbon monoxide sensor 214, combustible gas sensor 216, carbon dioxide sensor 218, and/or formaldehyde sensor 220.

In an additional and/or alternative aspect, server 108 can identify the fact that sensor component 106 has transmitted conflicting readings from two or more disparate sensors included in sensor component 106. Where server 108 ascertains that sensor component 106 has dispatched conflicting readings from two or more disparate sensors, server 108 can filter out the conflicting readings. Thus, through a filtering aspect, server 108 can filter out conflicting readings from two or more of particulate sensor 204, volatile organic compound sensor 210, nitrogen oxide sensor 212, carbon monoxide sensor 214, combustible gas sensor 216, carbon dioxide sensor 218, and/or formaldehyde sensor 220.

It should be noted that the sensors associated sensor component 106, in addition to those previously enunciated above, can also include optical sensors (e.g., infrared and/or ultraviolet sensors) and/or sonic sensors. Additionally and/or alternatively, passive radio sensors, such as sensors that sense radio frequency interactions with a microelectro mechanical system (MEMS), can also be associated or included with sensor component 106. Other sensors that can be associated or included with sensor component 106 can include light level sensors, vibration sensors, lead sensors, moisture sensors, image sensors, and the like.

In addition to the foregoing described sensors that sense air quality, sensor component 106 can also include sensors that measure noise levels. Noise level sensors can enable remote monitoring of the effect of outdoor noise (e.g., emanating from cars, trains, airplanes, etc.) and indoor noise (e.g., high occupancy, music, televisions, . . . ) on air quality and childhood development, for instance.

Prior to deployment and/or periodically over the life expectancy of air quality monitor 102, air quality monitor 102 and/or the sensors included within air quality monitor 102 can be subjected to calibration and/or re-calibration, wherein the sensors can be calibrated by individually placing the sensors, placing two or more sensors, or placing air quality monitor 102 in a calibration chamber wherein gases, such as, nitrogen oxide, carbon monoxide, carbon dioxide, hydrogen sulfide, volatile organic compounds, combustible gases, and the like can be introduced into the calibration chamber at identified levels. In response to the specified levels of introduced gases, the one or more sensors can react with an identifiable voltage level which can be noted and charted. Thus, a voltage level for a particular introduced gas can be associated with an identifiable concentration of gas, typically measured in parts per million (ppm) or parts per billion (ppb). The curves determined or ascertained from these calibration activities can be utilized by air quality monitor 102 and/or server 108 to provide indication of the air quality in the residential house.

Additionally and/or alternatively, because sensor accuracy drifts over time, a self calibration feature is provided wherein, once sensors have been deployed in the field, these sensors can be calibrated or recalibrated through communication with server 108, for example. Generally, where more up-to-date calibration curves have been obtained by server 108, for instance, through calibration activities as described above, these updated calibration curves can be supplied (through wireless or wired modalities) to the sensors associated with a remotely situated air quality monitor (e.g., air quality monitor 102 situated in a residential house).

In addition, in the context of calibration and re-calibration of sensors associated with deployed air quality monitors, measurements from various sensors deployed in one or more deployed air quality monitor located in a single residential house or multiple residential houses dispersed across various geographical areas can be employed for purposes of generating calibration curves that can be employed by server 108 for purposes of calibration and/or recalibration of sensors in deployed air quality monitors (e.g., air quality monitor 102). It should also be noted, that the calibration/recalibration of sensors in deployed air quality monitors can be automated.

Figure 3:
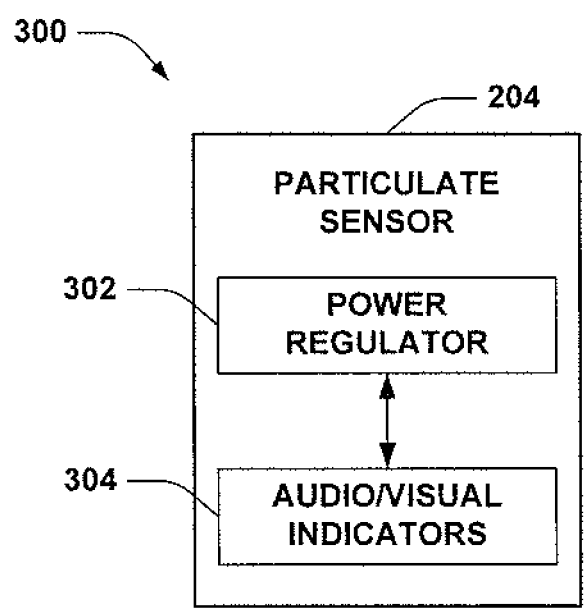
FIG. 3 provides a more detailed illustration of a particulate sensor in accordance with an aspect of the subject application.

FIG. 3 provides a more detailed illustration 300 of particulate sensor 204. As illustrated in FIG. 3 particulate sensor 204 can include power regulator 302 and audio/visual indicators 304. Power regulator 302 can be coupled to sensor power supply 202 and can regulate the power received from sensor power supply 202 to ensure that particulate sensor 204 operates within its specified power restrictions and requirements. Audio/visual indicators 304 associated with particulate sensor 204 can provide various alarms, buzzers, and/or visual indicators that can act as warning indicators. As will be appreciated by those of ordinary skill in the art, typical visual indicators can include light emitting diodes (LEDs). Audio/visual indicators 304 can be configured to alert a residential homeowner of an elevated level of air pollutant within a residential house, for instance.

Figure 4:
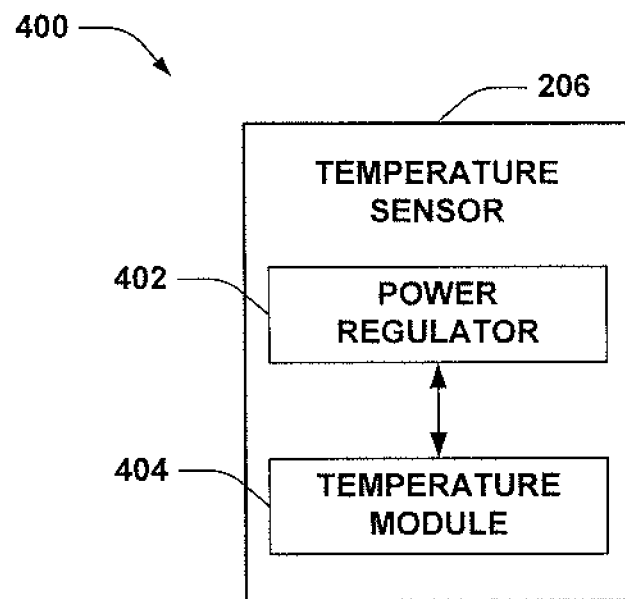
FIG. 4 provides a more detailed depiction of a temperature sensor in accordance with an aspect of the subject application.

FIG. 4 provides further illustration 400 of a temperature sensor 206. As illustrated temperature sensor 206 can include power regulator 402 and temperature module 404. As noted above, power regulator 402 can be coupled to sensor power supply 202 and can regulate the power requirements for operation of temperature module 404. Temperature module 404 can be a serially accessible digital temperature sensor, wherein temperature data is converted from an internal thermal sensing element and made available at any time as a 13-bit two's compliment digital word. Generally, temperature module 404 can have a 12-bit plus sign temperature resolution of 0.0625° C., Least Significant Bit. Typically, temperature module 404 can offer a temperature accuracy of ±1.0° C. over a temperature range of +25° C. to +65° C. When operational, temperature module 404 can consume approximately 250 µA. Additionally, temperature module 404 can include a configuration register that can be used to activate a low power shutdown mode that can have a current consumption of only 0.1 µA.

Figure 5:
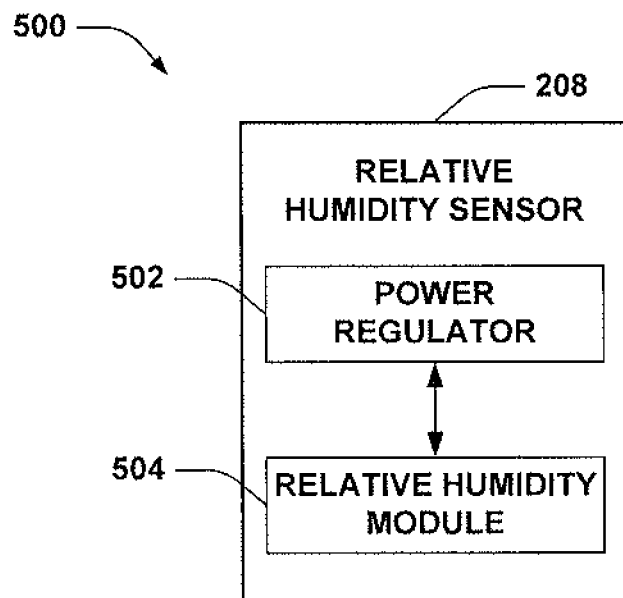
FIG. 5 provides further depiction of the relative humidity sensor in accordance with an aspect of the subject application.

FIG. 5 provides a more detailed illustration 500 of relative humidity sensor 208. As depicted relative humidity sensor 208 can include power regulator 502 and relative humidity module 504. As noted above in connection with power regulator 302 associated with particulate sensor 204, and power regulator 402 associated with temperature sensor 206, power regulator 502 can be coupled to sensor power supply 202 and can regulate the power requirements necessary for operation of relative humidity module 504. Relative humidity module 504 can be a covered integrated circuit humidity sensor. In accordance with an embodiment, relative humidity module 504 can be a covered, condensation-resistant, integrated circuit humidity sensor with a hydrophobic filter allowing it to be used in condensing environments including industrial, medical, and commercial applications. Relative humidity module 504 can use a laser trimmed, thermoset polymer capacitive sensing element with on-chip integrated signal conditioning. The sensing element's multilayer construction provides excellent resistance to most application hazards such as condensation, dust, dirt, oils, and, common environmental chemicals. A typical current draw for relative humidity module 504 can be in the range of about 200 µA.

Figure 6:
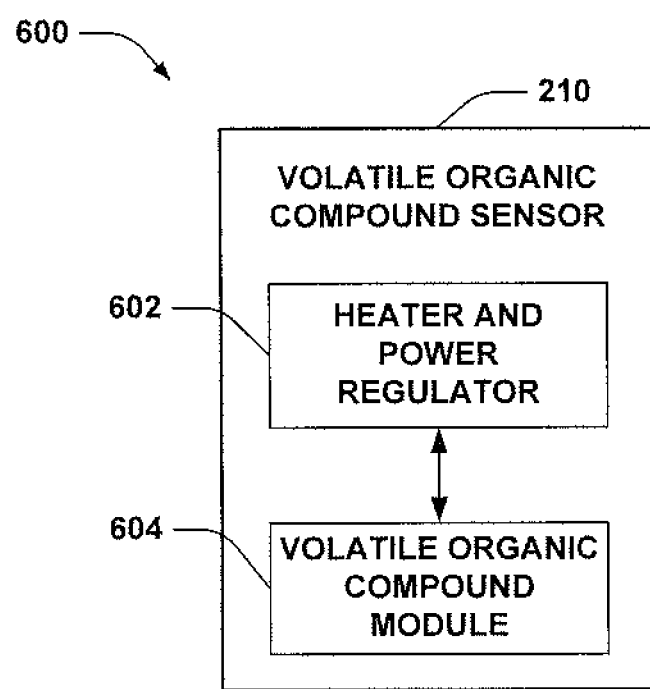
FIG. 6 provides illustration of a volatile organic compounds sensor in accordance with an aspect of the subject application.

FIG. 6 provides a more detailed illustration 600 of volatile organic compound sensor 210. Volatile organic compound sensor 210 can include heater and power regulator 602 and volatile organic compound module 604. Heater and power regulator 602 can be similarly configured to those describe above in connection with power regulators 302, 402, and 502 respectively associated with particulate sensor 204, temperature sensor 206, and relative humidity sensor 208. Accordingly, in order to avoid needless prolixity further discussion on the aspects included with heater and power regulator 602 has been omitted. Volatile organic compound module 604 can be a sensing element comprised of a metal oxide semiconductor layer formed on an alumina substrate of a sensing chip together with an integrated heater. In the presence of a detectable gas, sensor conductivity can increase depending on gas concentrations in the air. A simple electrical circuit can convert the change in conductivity to an output signal that typically corresponds to the gas concentration. Generally, volatile organic compound module 604 can have a high sensitivity to low concentrations of odorous gases, such as ammonia and hydrogen sulfide generated from waste materials typically found in an office and home environments. Further, volatile organic compound module 604 can also have high sensitivity to low concentrations of volatile organic compounds, such as toluene emitted from wood finishing and construction products.

Figure 7:
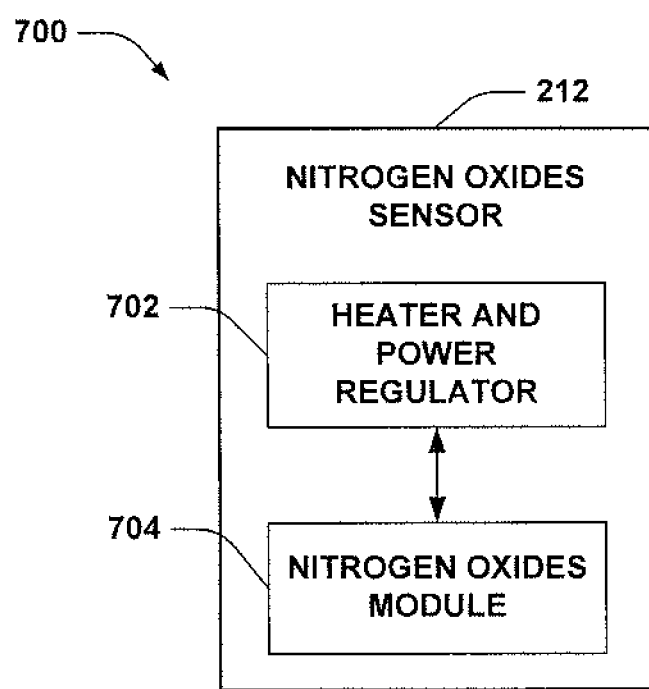
FIG. 7 provides illustration of a nitrogen oxides sensor in accordance with an aspect of the subject application.

FIG. 7 provides a more detailed illustration 700 of nitrogen oxides sensor 212. Nitrogen oxides sensor 212 as depicted in FIG. 7 can include heater and power regulator 702, and nitrogen oxides module 704. As described above in relation to the heater and power regulator 602 associated with volatile organic compound sensor 210, heater and power regulator 702 can be utilized and configured in a manner similar to that described in connection with heater and power regulator 602. Nitrogen oxides module 704 can be a sensor that detects very low concentrations of nitrogen oxides, typically in the range from 0.5 ppm to 10 ppm, for instance. Where larger dynamic detection ranges are required (e.g., in the range from 5 ppm to 100 ppm) nitrogen oxides module 704 can utilize the facilities of an integrated heater. Generally, nitrogen oxides module 704 can be operational within an environmental temperature range from 20° C. to 50° C. (and typically from less than or equal to 20° C. to in excess of 50° C.) and an environmental humidity range from 0 to 90% relative humidity, non-condensing.

Figure 8:
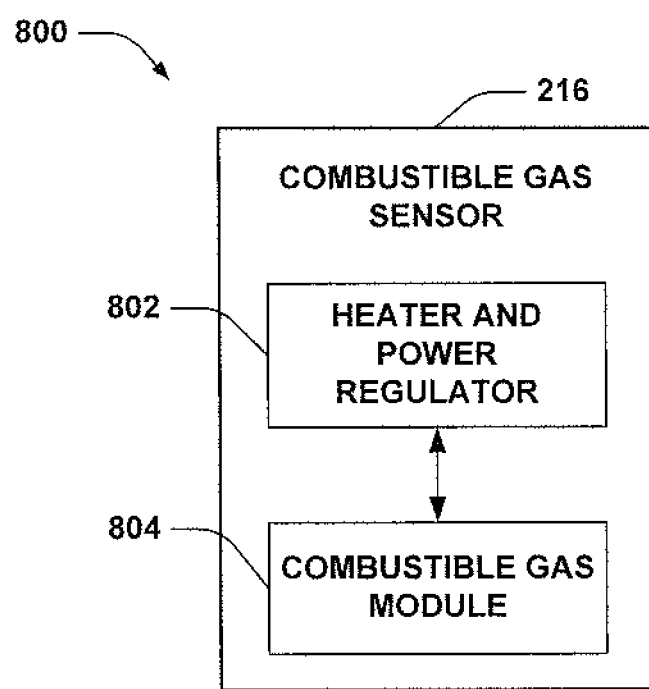
FIG. 8 provides a more detailed depiction of a combustible gas sensor in accordance with an aspect of the subject application.

FIG. 8 provides a more detailed illustration 800 of combustible gas sensor 216. As illustrated in FIG. 8 combustible gas sensor 216 can include heater and power regulator 802 that can be configured in a manner similar to that described and disclosed above in relation to heater and power regulator 702 associated with nitrogen oxides sensor 212. Additionally, combustible gas sensor 216 can include combustible gas module 804 can be a sensor that detects very low concentrations of combustible gases, typically in the range of less than 0.5 ppm to in excess of 10 ppm, for example. Combustible gas module 804, like nitrogen oxides module 704, discussed above, can be augmented with a heating aspect. Such a heating aspect can be particularly useful and/or beneficial where larger dynamic detection ranges are required.

Figure 9:
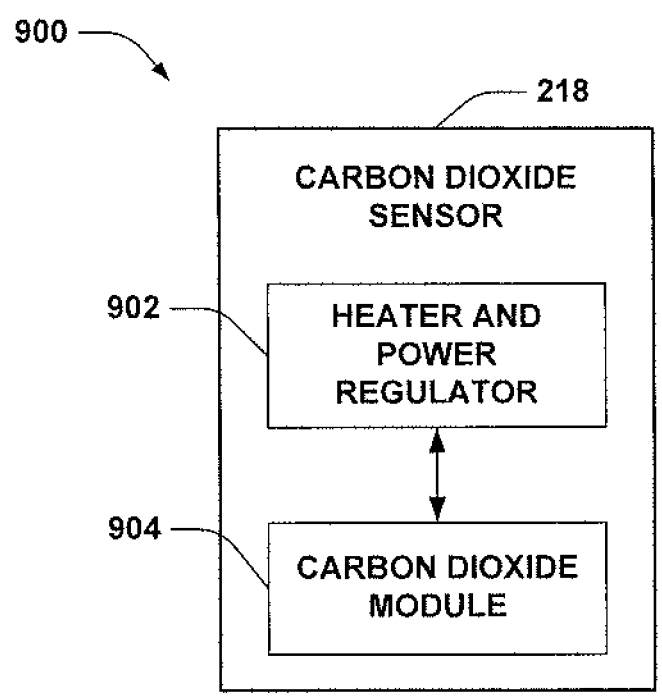
FIG. 9 provides a more detailed illustration of a carbon dioxide sensor in accordance with an aspect of the subject application.

FIG. 9 provides a more detailed depiction 900 of carbon dioxide sensor 218. As depicted in FIG. 9 carbon dioxide sensor 218 can include heater and power regulator 902 that can be configured in a manner similar to that described and disclosed in relation to heater and power regulator 802 associated with combustible gas sensor 216 and heater and power regulator 702 associated with nitrogen oxides sensor 212. Further, carbon dioxide sensor 218 can also include carbon dioxide module 904 that can be a sensor that detects very low concentrations of carbon dioxide, typically in the range from 0.5 ppm to 10 ppm. Where larger dynamic detection ranges are necessary (e.g., in a range from 5 ppm to 100 ppm) carbon dioxide module 904 can be augmented with a heating element (e.g., a heater). Typically, carbon dioxide module 904 can be operational within an environmental temperature range from 20° C. to 50° C. (and typically from less than or equal to 20° C. to in excess of 50° C.) and an environmental humidity range of between 0 to 90% relative humidity, non-condensing.

Figure 10:
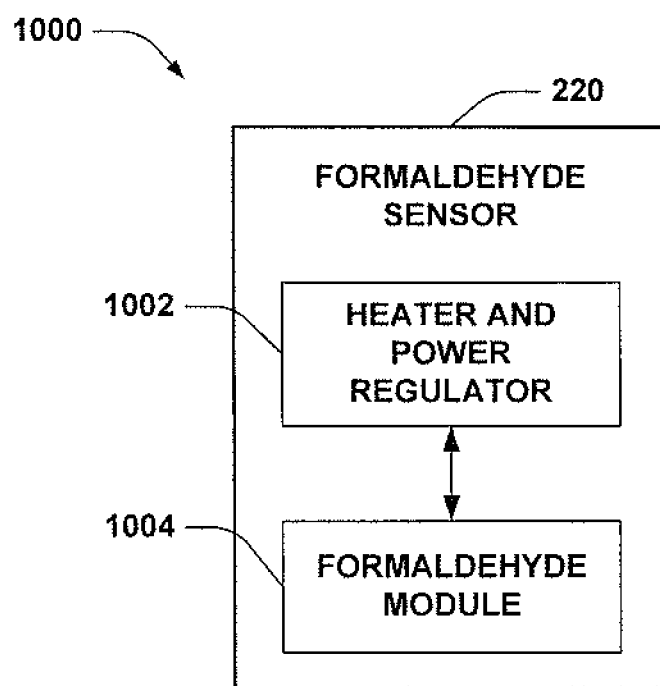
FIG. 10 provides a more detailed depiction of a formaldehyde sensor in accordance with an aspect of the subject application.

FIG. 10 provides a more detailed depiction 1000 of formaldehyde sensor 220. As illustrated, formaldehyde sensor 220 can include heater and power regulator 1002. Heater and power regulator 1002 can be configured and operate in a manner previously described in the context of heater and power regulator 902 associated with carbon dioxide sensor 218, accordingly for the sake of brevity further description and disclosure of such aspects associated with heater and power regulator 1002 have been omitted. Also as illustrated in FIG. 10 formaldehyde sensor 220 can include formaldehyde module 1004. Formaldehyde module 1004 can be a sensing element comprised of a metal oxide semiconductor layer formed on an alumina substrate of a sensing chip together with an integrated heater. In the presence of a detectable gas, sensor conductivity can increase depending on gas concentrations in the air. A simple electrical circuit can convert the change into conductivity to an output signal that can correspond to the gas concentration. Generally, formaldehyde module 1004 can have high sensitivity to low concentrations of gases, such as ammonia, hydrogen sulfide, and volatile organic compounds such as toluene that can typically be emitted from wood finishing and construction products.

Figure 11:
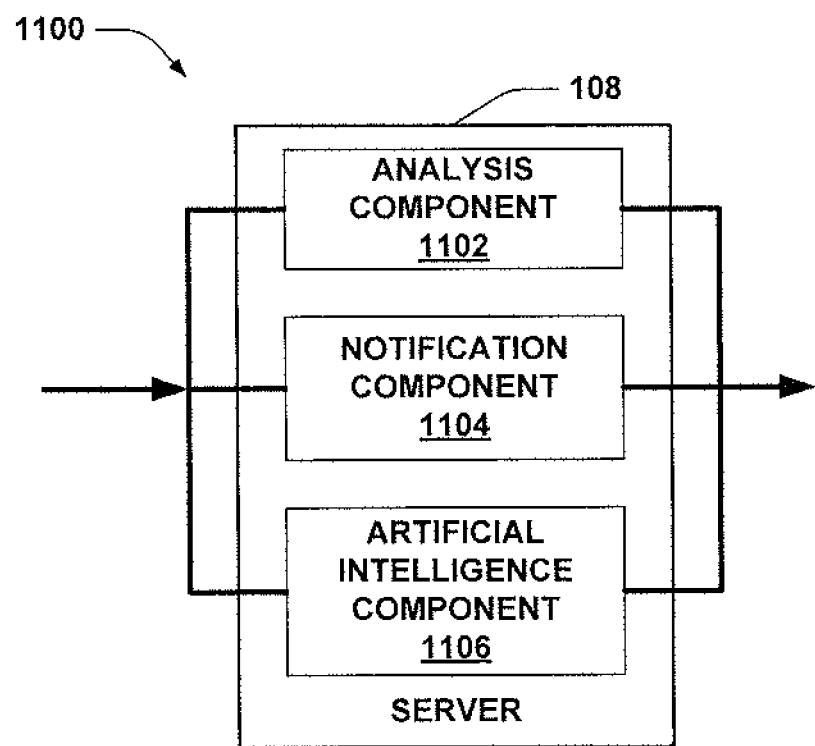
FIG. 11 provides a more detailed depiction of a server in accordance with an aspect of the subject application.

FIG. 11 provides a more detailed illustration 1100 of server 108. As illustrated, server 108 can include analysis component 1102, notification component 1104, and artificial intelligence component 1106. Analysis component 1102 can receive various data points from air quality monitor 102 that can be in wireless communication with server 108. Analysis component 1102, upon receipt of the various data points from air quality monitor 102, can construct or build an environmental fingerprint associated with the residential house within which air quality monitor 102 is positioned. As has been noted above, the environmental fingerprint associated with the residential house will typically be unique. In addition, to the various data points received from air quality monitor 102, analysis component 1102 can also utilize information retrieved from an associated data store or database (e.g., database or data store 110) to generate or create the environmental fingerprint associated with the residential house. Typical information that can be retrieved by analysis component 1102 from the associated data store or database can include information associated with thresholds (minimum or maximum) beyond which human health can be affected. Generally, these thresholds are related to air quality metrics.

Analysis component 1102, having established a baseline or initial environmental fingerprint for the residential house within which air quality monitor 102 has been located, can effectuate a comparison between the baseline or initial environmental fingerprint and a dynamically or continuously updated environmental fingerprint for the residential house. In this manner, analysis component 1102 can monitor trends (increases or decreases) in pollution levels within the residential house.

In accordance with an embodiment, analysis component 1102 can develop a graph that outlines the trends in each respective pollutant monitored by air quality monitor 102. In accordance with this embodiment, analysis component 1102 can plot the rise or fall of an air pollutant level over time. Where analysis component 1102 notes an upward or downward deviation between the level of the air pollutant and the determined environmental fingerprint associated with the residential house, analysis component 1102 can, through facilities provided by notification component 1104, broadcast a notification to a homeowner or user that he/she should take remedial actions to abate the upward or downward deviation in the level of air pollutant extant within the residential house.

Additionally and/or alternatively, where analysis component 1102 notes an upward or downward deviation between the level of the air pollutant and the environmental fingerprint associated with the residential house, analysis component 1102, once again utilizing facilities provided by notification component 1104, can broadcast or dispatch a notification signal or message directly to the air quality monitor 102, wherein the notification signal or message causes the air quality monitor 102 to activate one or more audio/visual warning indicators, such as alarms, buzzers, and/or flashing light emitting diodes (LEDs), associated with air quality monitor 102.

In accordance with a further aspect, analysis component 1102 can compare the level of an air pollutant against a threshold deviation value that can be a function of the environmental fingerprint associated with the residential house, and in response to the level of the air pollutant exceeding or failing to meet the threshold deviation, server 108, through mechanisms provided by notification component 1104, can broadcast a notification to the air quality monitor 102 that it (e.g., air quality monitor 102) should activate one or more audio/visual warning indicators as described above. In a similar manner, analysis component 1102 can also compare the level of the air pollutant against a threshold deviation value that can be a function of the ascertained environmental fingerprint associated with the residential house, and in response to the level of the air pollutant exceeding or falling below the threshold deviation, server 108, using facilities provided by notification component 1104, can broadcast a notification to the residential homeowner or the user that he/she should take remedial measures to ensure the evacuation of the air pollutant from the residential house.

As has been noted above, server 108 can include notification component 1104 that can broadcast a notification to the residential homeowner or the user that he/she should take remedial measures to ensure the evacuation of an air pollutant from the residential house. Additionally and/or alternatively, notification component 1104 can broadcast a notification to air quality monitor 102 that it should activate one or more audio/visual warning indicators thereby raising an alarm to inform the homeowner or persons living within the residential house that air borne pollution levels have reached hazardous levels and that they should perform actions to avoid the pollution (e.g., by moving into an area of the residential house that has a more salubrious air quality environment). Typically, notification component 1104 can dispatch or broadcast messages and/or signals using e-mail, the short message service, multimedia messaging service, a paging service, or any one of a number of other communications techniques.

In context of building, constructing, and/or establishing an environmental fingerprint unique to the residential house within which air quality monitor 102 is placed, analyzing data received from air quality monitor 102, and/or ascertaining whether or not air pollutant levels within the residential house have exceeded or fallen below acceptable threshold levels and/or have experienced rates of change that indicate that the environment within the residential house have become less than tolerable, analysis component 1102 can be aided through utilization of one or more artificial intelligence and/or machine learning techniques and/or technologies that can be included within artificial intelligence component 1106. For instance, artificial intelligence component 1106 can employ artificial intelligence and/or machine learning techniques and/or technologies that employ probabilistic-based or statistical-based approaches, for example, in connection with making determinations or inferences. Inferences can be based at least in part on explicit training of classifiers or implicit training based at least in part upon system feedback and/or a users' or a systems' previous actions, commands, instructions, and the like. The intelligence functionalities and features utilized by server 108 can employ any suitable scheme (e.g., neural networks, expert systems, Bayesian belief networks, support vector machines (SVMs), Hidden Markov Models (HMMs), fuzzy logic, data fusion, etc.) in accordance with implementing various automated aspects described herein. Additionally, artificial intelligence component 1106 can further factor historical data, extrinsic data, context, data content, state of the user, and can compute costs of making an incorrect determination or inference versus benefits of making a correct determination or inference. Accordingly, a utility-based analysis can be employed with providing such information to other components or taking automated action. Ranking and confidence measures can also be calculated and employed in connection with such analysis.

Server 108, and in particular analysis component 1102, notification component 1104, and artificial intelligence component 1106 can further include utilization of other components (not shown) that take advantage of information fission which may be inherent to a process (e.g., receiving and/or deciphering inputs) relating to analyzing inputs through several different sensing modalities. In particular, one or more available inputs may provide a unique window into a physical environment (e.g., an entity inputting instructions) through several different sensing or input modalities. Because complete details of the phenomena to be observed or analyzed may not be contained within a single sensing/input window, there can be information fragmentation which can result from this fission process. These information fragments associated with the various sensing devices can include both independent and dependent components.

The independent components can be used to further fill out (or span) an information space, and the dependent components can be employed in combination to improve quality of common information recognizing that all sensor/input data can be subject to error, and/or noise. In this context, data fusion techniques employed by the components included in server 108 can include algorithmic processing of sensor/input data to compensate for inherent fragmentation of information because particular phenomena may not be observed directly using a single sensing/input modality. Thus, data fusion provides a suitable framework to facilitate condensing, combining, evaluating, and/or interpreting the available sensed or received information in the context of a particular application.

Moreover, server 108 and its included components (e.g., analysis component 1102, notification component 1104, and artificial intelligence component 1106) can also include utilization of one or more synthesizing aspects to combine, or filter information received from a variety of inputs (e.g., text, speech, gaze, environment, audio, images, gestures, noise, temperature, touch, smell, analog signals, digital signals, vibration, motion, altitude, location, GPS, wireless, . . . ), in raw or parsed (e.g., processed) form. Such synthesizing aspects, through combining and filtering, can provide a set of information that can be more informative or accurate than information from just one or two modalities, for example. As discussed with respect to the data fusion aspects above, which can be employed to learn correlations between different data types, the synthesizing functionalities can employ such correlations in connection with combining, or filtering the input data.

Additionally, server 108 can include aspects that determine context associated with a particular action or set of input data. As can be appreciated, context can play an important role with respect to understanding meaning associated with particular sets of input or intent of an individual or entity. For example, many words or sets of words can have double meanings (e.g. double entendre), and without proper context of use or intent of the words the corresponding meaning can be unclear thus leading to increased probability of error in connection with interpretation or translation thereof. Accordingly, the context determining aspects associated with server 108 can provide current or historical data in connection with inputs to increase proper interpretation of inputs. For example, time of day may be helpful to understanding and input—in the morning, the word "drink" would likely have a high probability of being associated with coffee, tea, or juice as compared to being associated with a soft drink or alcoholic beverage during the later hours. Context can also assist in interpreting uttered words that sound the same (e.g. homonyms). For instance, knowledge that it is near the dinnertime of a user as compared to the user camping would greatly help in recognizing the following spoken words "I need a steak/stake".

Figure 12:
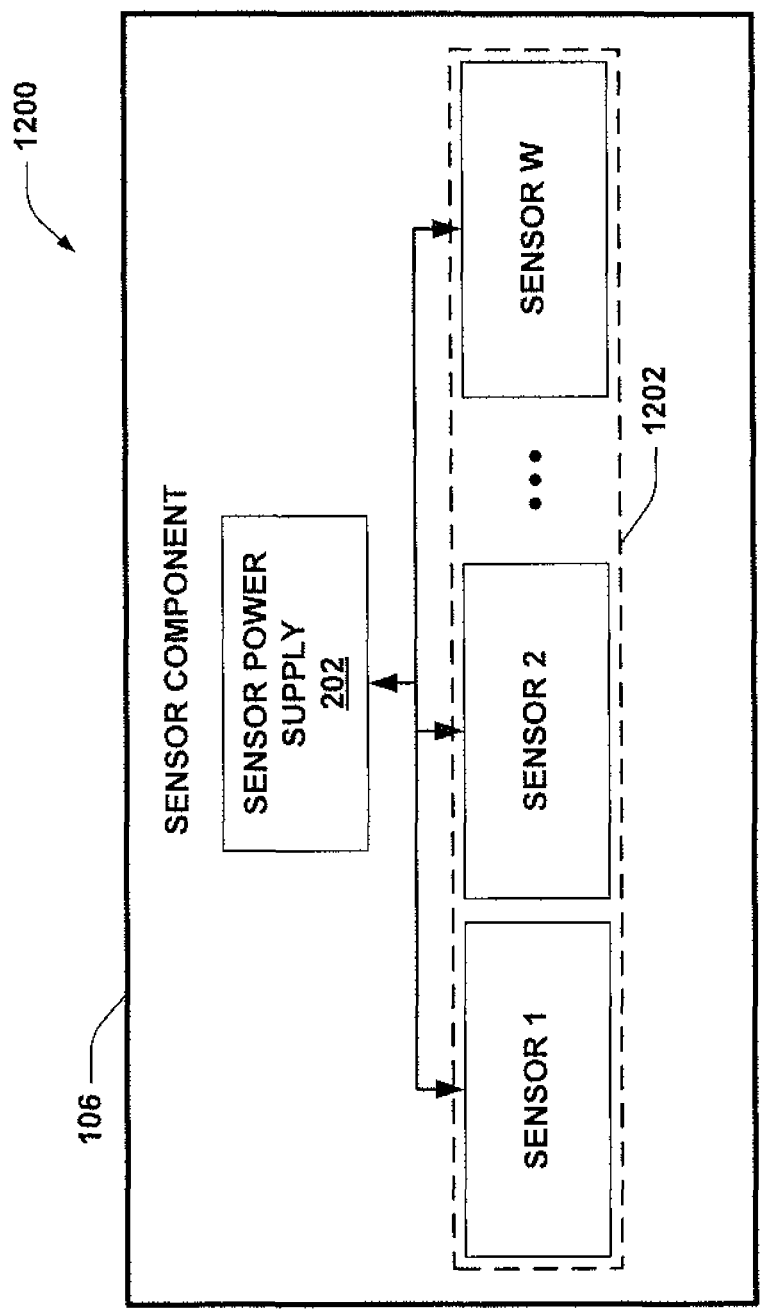
FIG. 12 provides further depiction of a sensor component in accordance with an aspect of the subject application.

FIG. 12 provides further depiction 1200 of a sensor component 106 in accordance with a further embodiment. As depicted, sensor component 106 can include sensor power supply 202 that, as enunciated above in the context of FIG. 2, can be configured to provide power to the various included aspects of the assorted sensors comprising sensor component 106. Typical sensors that can be included in sensor component 106 can include particulate sensors, temperature sensors, relative humidity sensors, volatile organic compound sensors, nitrogen oxide sensors, carbon monoxide sensors, combustible gas sensors, carbon dioxide sensors, formaldehyde sensors, and the like. The noted sensors can each be coupled to sensor power supply 202 whereupon sensor power supply 202 can satisfy the power requirements for each of the included sensors. As has already been noted, the power requirements for each of the included sensors can differ markedly; as a consequence sensor power supply 202 can satisfy and adjust the supply of power to meet the disparate power needs of each and every sensor included in sensor component 106.

As is noted above, sensor component 106 can include a multiplicity of sensors, typically, and as depicted in FIG. 12, the multiplicity of sensors can include at least a first sensor (e.g., sensor 1) and a second sensor (e.g., sensor 2). Generally, the first sensor (sensor 1) can comprise at least one of a particulate sensor, a temperature sensor, a relative humidity sensor, a volatile organic compound sensor, a nitrogen oxides sensor, a carbon monoxide sensor, a combustible gas sensor, or a carbon dioxide sensor, and/or the second sensor (sensor 2) can comprise at least one of a temperature sensor, a relative humidity sensor, a volatile organic compound sensor, a nitrogen oxides sensor, a carbon monoxide sensor, a combustible gas sensor, a carbon dioxide sensor, or a formaldehyde sensor, to enumerate but a few sensors that can be included within sensor component 106. Additionally and/or alternatively, one or more additional sensors (sensor w) can also be included; these one or more additional sensors can include other sensors that can monitor/sense the ambient environment. As depicted in FIG. 12, sensor 1, sensor 2, . . . , sensor w have been grouped together and are referred to as sensors 1202.

Sensors 1202, in accordance with a further embodiment, can include a particulate sensor as sensor 1 and a temperature sensor as sensor 2. In accordance with another embodiment, sensors 1202 can include a particulate sensor as sensor 1, a temperature sensor as sensor 2, and one or more of a relative humidity sensor, a volatile organic compound sensor, a nitrogen oxides sensor, a carbon monoxide sensor, a combustible gas sensor, a carbon dioxide sensor, or a formaldehyde sensor as sensor w. In accordance with yet another embodiment, sensors 1202 can include two or more of particulate sensor, temperature sensor, relative humidity sensor, volatile organic compound sensor, nitrogen oxide sensor, carbon monoxide sensor, combustible gas sensor, carbon dioxide sensor, and/or formaldehyde sensor as sensor 1 and sensor 2. In accordance with yet a further embodiment, sensors 1202 can include at least two sensors that include particulate sensor, temperature sensor, relative humidity sensor, volatile organic compound sensor, nitrogen oxide sensor, carbon monoxide sensor, combustible gas sensor, carbon dioxide sensor, and/or formaldehyde sensor as sensor 1, sensor 2, . . . , sensor w. It should be noted in regard to the foregoing, that the sensors disclosed and discussed herein are not limited to particulate sensors, temperature sensors, relative humidity sensors, volatile organic compound sensors, nitrogen oxide sensors, carbon monoxide sensors, combustible gas sensors, carbon dioxide sensors, and/or formaldehyde sensors. As will be appreciated by those of ordinary skill in the art, other sensors equally capable of monitoring/sensing the ambient environment can also be utilized with similar facility and/or utility.

It should be noted in connection with the aforementioned described and disclosed features, aspects, structures, characteristics, and/or embodiments pertaining to air quality monitor 102 (and its components: radio module 104 and sensor component 106) and server component 108 (and its components: analysis component 1102, notification component 1104, and artificial intelligence component 1106) that these features, aspects, structures, characteristics, and/or embodiments can be combined and/or interchanged in any suitable manner to form one or more further embodiments without departing from the spirit and intent of the subject application. For example, air quality monitor 102 can include components that can undertake the functionalities performed by server component 108. Thus, air quality monitor 102 can include an aspect that performs analysis of input received from the one or more sensors included with sensor component 106. Further, air quality monitor 102 can also include aspects that broadcast notifications to relevant personnel (e.g., homeowners, healthcare providers, researchers, etc.). Additionally, air quality monitor 102 can include functionalities the can undertake the above described features performed by artificial intelligence component 1106 located with server 108. Similarly, server 108 can perform the functionalities and facilities provided by air quality monitor 102. Thus, for example, server 108 can receive input broadcast directly from sensors dispersed throughout a habitable area/space and thereafter process and activate one or more abatement devices (e.g., air purifiers, mass air extraction devices, ventilators, and the like) that can also be located in the habitable area/space.

Figure 13:
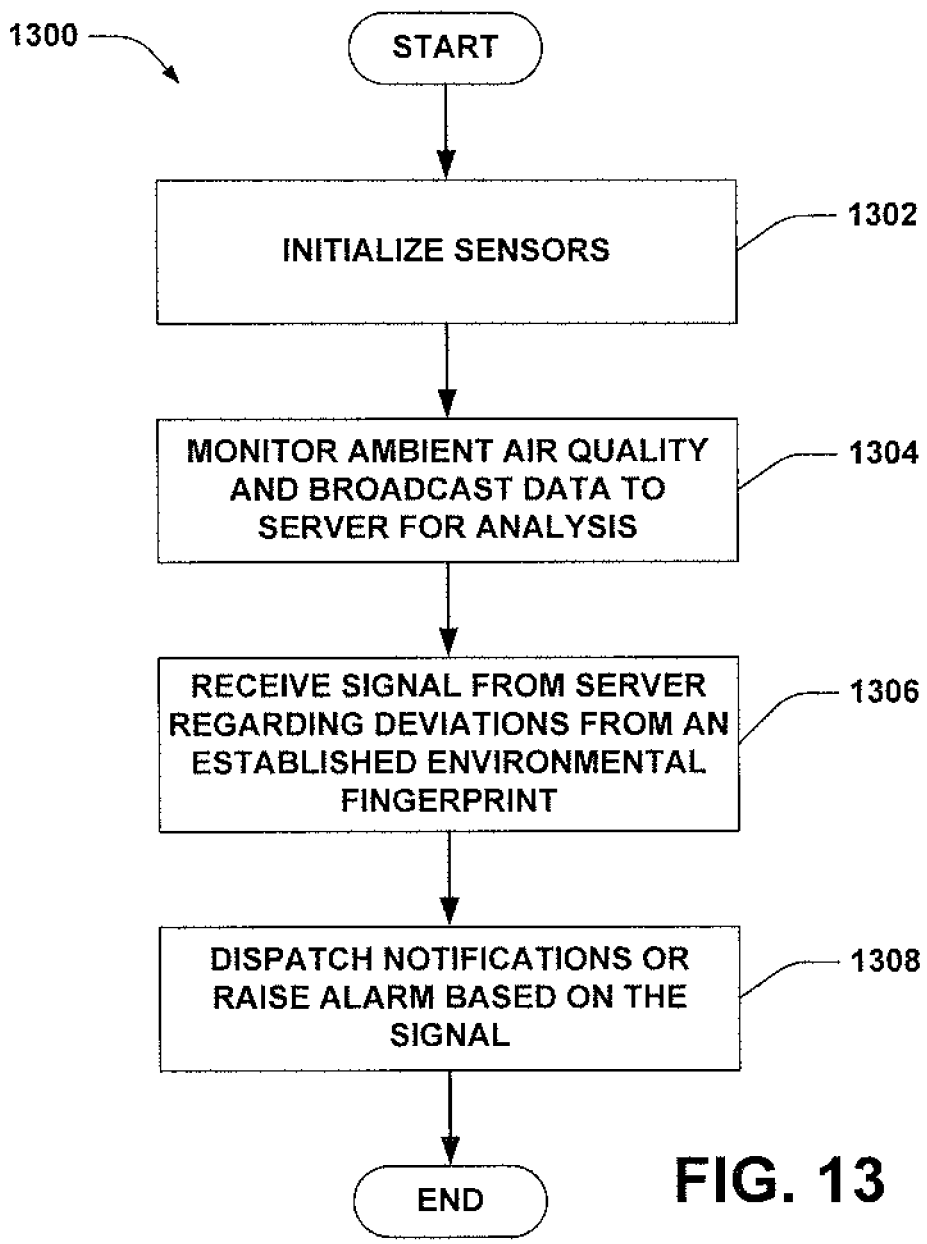
FIG. 13 illustrates a method for monitoring residential air quality and providing trend based analysis in regard to various air pollutants.
Figure 14:
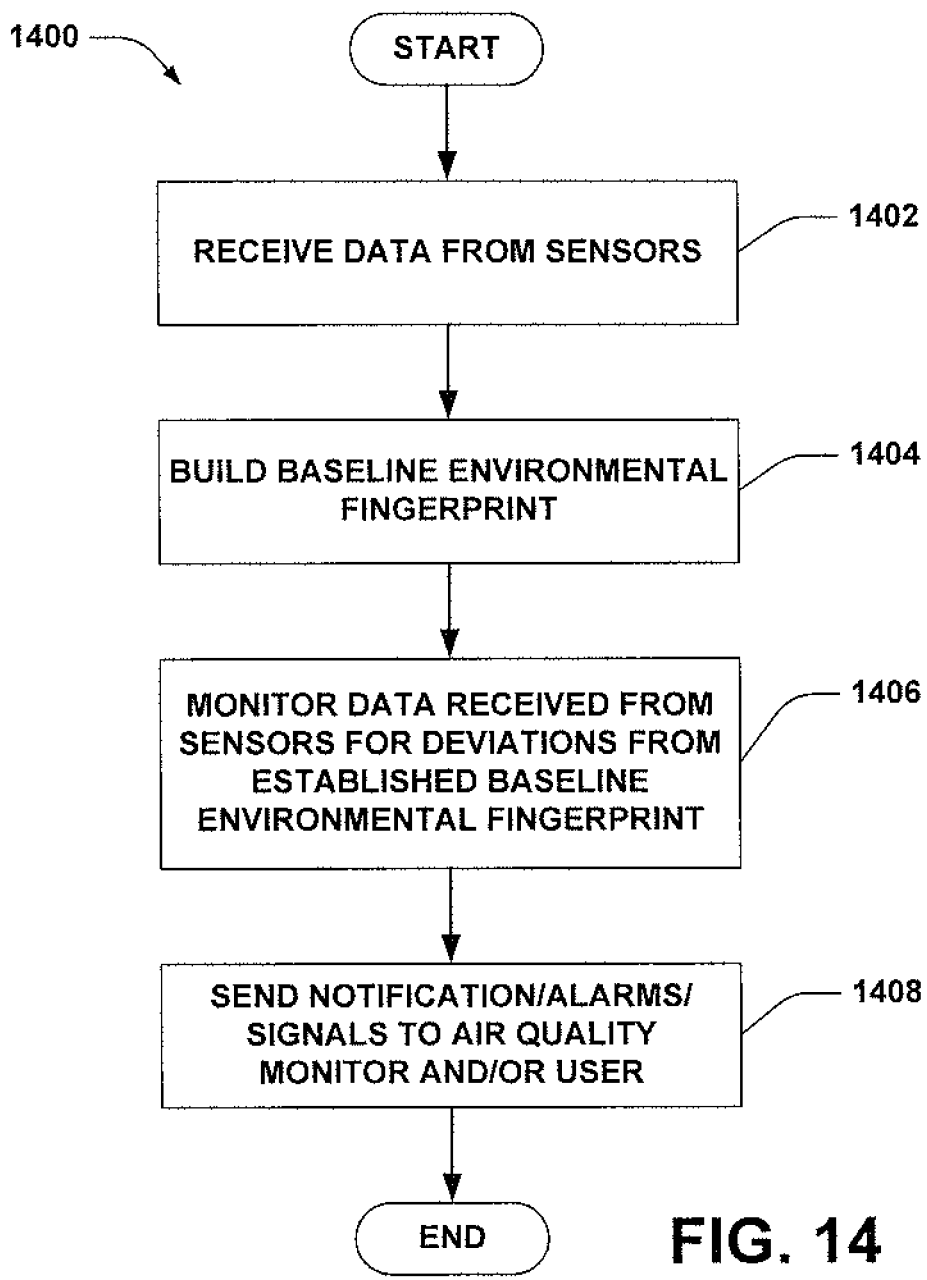
FIG. 14 illustrates a further method for monitoring residential air quality and providing trend based analysis and/or notification in regard to various air pollutants.

FIGS. 13-14 illustrate methodologies in accordance with the disclosed subject matter. For simplicity of explanation, the methodologies are depicted and described as a series of acts. It is to be understood and appreciated that the subject application is not limited by the acts illustrated and/or by the order of acts. For example, acts can occur in various orders and/or concurrently, and with other acts not presented or described herein. Furthermore, not all illustrated acts may be required to implement the methodology in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

FIG. 13 provides an illustrative method 1300 for monitoring residential air quality and providing trend based analysis in regard to various air pollutants, such as airborne particulate matter, volatile organic compounds, nitrogen oxides, carbon monoxide, combustible gases, carbon dioxide, and/or formaldehyde. Method 1300 can commence at 1302 where various sensors included in an air quality monitor (e.g., air quality monitor 102) can be initialized. At 1304 an air quality monitor (e.g., air quality monitor 102) can monitor the ambient air quality and broadcast data to a server (e.g., server 108) for analysis and/or trend monitoring. At 1306 messages or signals can be received from the server (e.g., server 108) regarding deviations from an established environmental fingerprint, wherein the established environmental fingerprint is associated with a residential house within which the air quality monitor (e.g., air quality monitor 102) is located and the established environmental fingerprint is created or constructed by the server (e.g., server 108) from readings dispatched by the air quality monitor. At 1308 notifications can be broadcast or dispatched to various components (e.g., particulate sensor 204, temperature sensor 206, relative humidity sensor 208, volatile organic compound sensor 210, nitrogen oxides sensor 212, carbon monoxide sensor 214, combustible gas sensor 216, carbon dioxide sensor 218, and/or formaldehyde sensor 220) associated with the air quality monitor (e.g., air quality monitor 102), whereupon various alarms, buzzers, and light emitting diodes (LEDs) can be activated. Additionally, notifications can be sent to a user or the residential homeowner to provide them information regarding how to bring the air pollutant levels within the bounds of prescribed or established environmental fingerprint established for the residential house.

FIG. 14 provides a further illustrative method 1400 for monitoring residential air quality and providing trend based analysis in regard to various air pollutants. Method 1400 can commence at 1402 whereupon a server (e.g. server 108) can receive data from one or more sensors included in an air quality monitor (e.g., air quality monitor 102). At 1404 the server can build a baseline environmental fingerprint for the residential house within which the air quality monitor has been positioned. At 1406 the server can continuously monitor the data received from the one or more sensors included in the air quality monitor to ascertain deviations from the established baseline environmental fingerprint created for the residential house. Where the server identifies an upward or downward trend in the air pollutant levels established as the baseline environmental fingerprint for the residential house it can dispatch or send notifications, alarms, signals, messages, etc. to the air quality monitor and/or to the homeowner or user, making the homeowner or user aware that the air pollution levels within the residential house has become deleteriously contaminated or polluted and that the homeowner or user should take steps to abate the problem.

As it is employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions and/or processes described herein. Processors can exploit nano-scale architectures such as, but not limited to, molecular and quantum-dot based transistors, switches and gates, in order to optimize space usage or enhance performance of mobile devices. A processor may also be implemented as a combination of computing processing units.

In the subject specification, terms such as "store," "data store," "data storage," "database," "storage medium," and substantially any other information storage component relevant to operation and functionality of a component and/or process, refer to "memory components," or entities embodied in a "memory," or components comprising the memory. It will be appreciated that the memory components described herein can be either volatile memory or nonvolatile memory, or can include both volatile and nonvolatile memory.

By way of illustration, and not limitation, nonvolatile memory, for example, can be included in storage systems described above, non-volatile memory 1522 (see below), disk storage 1524 (see below), and memory storage 1546 (see below). Further, nonvolatile memory can be included in read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Figure 15:
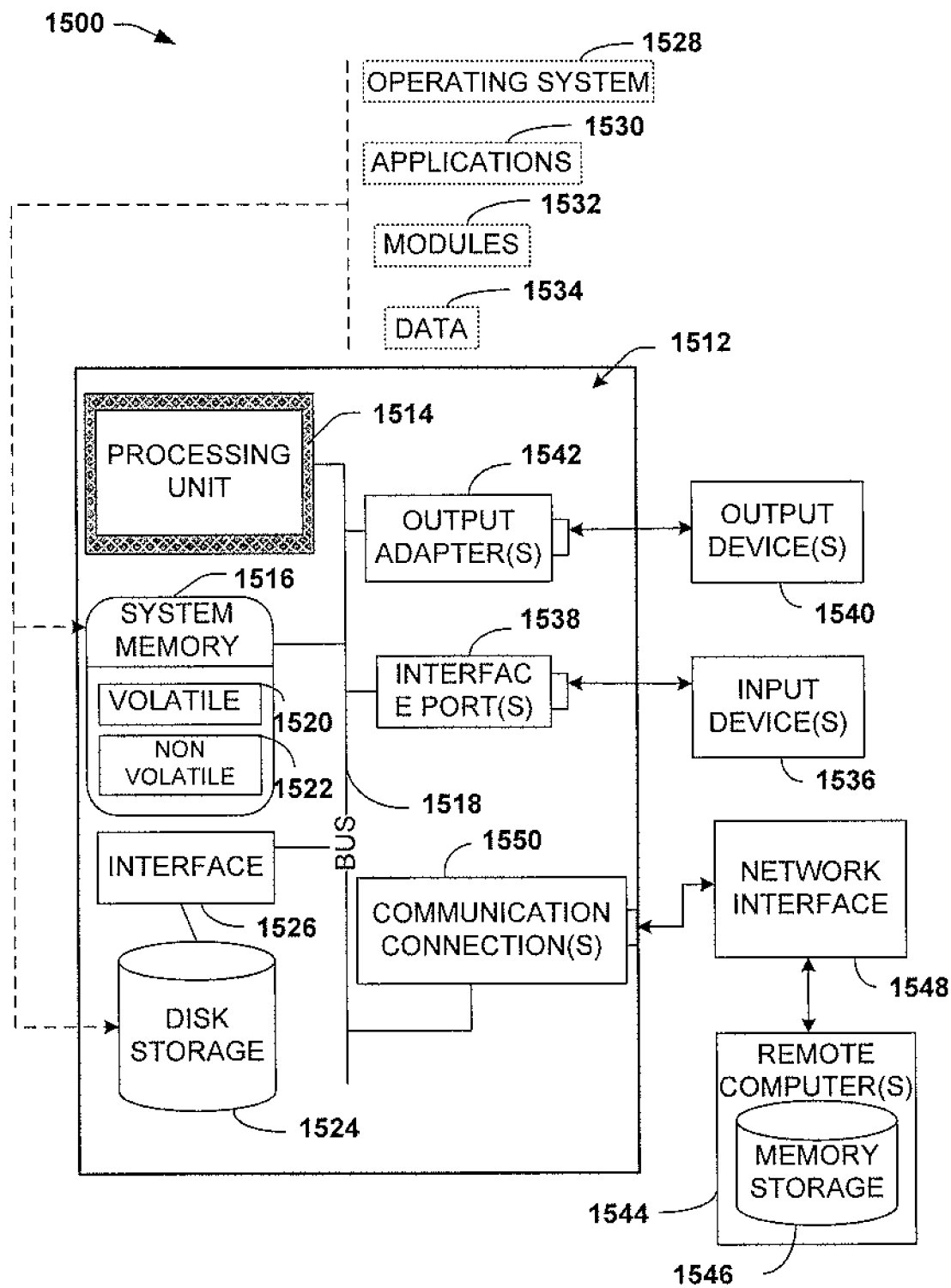
FIG. 15 illustrates a block diagram of a computing system operable to execute the disclosed systems and methods, in accordance with an embodiment.

In order to provide a context for the various aspects of the disclosed subject matter, FIG. 15, and the following discussion, are intended to provide a brief, general description of a suitable environment in which the various aspects of the disclosed subject matter can be implemented, e.g., various processes associated with FIGS. 1-14. While the subject matter has been described above in the general context of computer-executable instructions of a computer program that runs on a computer and/or computers, those skilled in the art will recognize that the subject application also can be implemented in combination with other program modules. Generally, program modules include routines, programs, components, data structures, etc. that perform particular tasks and/or implement particular abstract data types.

Moreover, those skilled in the art will appreciate that the inventive systems can be practiced with other computer system configurations, including single-processor or multiprocessor computer systems, mini-computing devices, mainframe computers, as well as personal computers, handheld computing devices (e.g., PDA, phone, watch), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

With reference to FIG. 15, a block diagram of a computing system 1500 operable to execute the disclosed systems and methods is illustrated, in accordance with an embodiment. Computer 1512 includes a processing unit 1514, a system memory 1516, and a system bus 1518. System bus 1518 couples system components including, but not limited to, system memory 1516 to processing unit 1514. Processing unit 1514 can be any of various available processors. Dual microprocessors and other multiprocessor architectures also can be employed as processing unit 1514.

System bus 1518 can be any of several types of bus structure(s) including a memory bus or a memory controller, a peripheral bus or an external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1194), and Small Computer Systems Interface (SCSI).

System memory 1516 includes volatile memory 1520 and nonvolatile memory 1522. A basic input/output system (BIOS), containing routines to transfer information between elements within computer 1512, such as during start-up, can be stored in nonvolatile memory 1522. By way of illustration, and not limitation, nonvolatile memory 1522 can include ROM, PROM, EPROM, EEPROM, or flash memory. Volatile memory 1520 includes RAM, which acts as external cache memory. By way of illustration and not limitation, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1512 can also include removable/non-removable, volatile/non-volatile computer storage media, networked attached storage (NAS), e.g., SAN storage, etc. FIG. 15 illustrates, for example, disk storage 1524. Disk storage 1524 includes, but is not limited to, devices like a magnetic disk drive, floppy disk drive, tape drive, Jaz drive, Zip drive, LS-100 drive, flash memory card, or memory stick. In addition, disk storage 1524 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1524 to system bus 1518, a removable or non-removable interface is typically used, such as interface 1526.

It is to be appreciated that FIG. 15 describes software that acts as an intermediary between users and computer resources described in suitable operating environment 1500. Such software includes an operating system 1528. Operating system 1528, which can be stored on disk storage 1524, acts to control and allocate resources of computer 1512. System applications 1530 take advantage of the management of resources by operating system 1528 through program modules 1532 and program data 1534 stored either in system memory 1516 or on disk storage 1524. It is to be appreciated that the disclosed subject matter can be implemented with various operating systems or combinations of operating systems.

A user can enter commands or information into computer 1512 through input device(s) 1536. Input devices 1536 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to processing unit 1514 through system bus 1518 via interface port(s) 1538. Interface port(s) 1538 include, for example, a serial port, a parallel port, a game port, and a universal serial bus (USB). Output device(s) 1540 use some of the same type of ports as input device(s) 1536.

Thus, for example, a USB port can be used to provide input to computer 1512 and to output information from computer 1512 to an output device 1540. Output adapter 1542 is provided to illustrate that there are some output devices 1540 like monitors, speakers, and printers, among other output devices 1540, which use special adapters. Output adapters 1542 include, by way of illustration and not limitation, video and sound cards that provide means of connection between output device 1540 and system bus 1518. It should be noted that other devices and/or systems of devices provide both input and output capabilities such as remote computer(s) 1544.

Computer 1512 can operate in a networked environment using logical connections to one or more remote computers, such as remote computer(s) 1544. Remote computer(s) 1544 can be a personal computer, a server, a router, a network PC, a workstation, a microprocessor based appliance, a peer device, or other common network node and the like, and typically includes many or all of the elements described relative to computer 1512.

For purposes of brevity, only a memory storage device 1546 is illustrated with remote computer(s) 1544. Remote computer(s) 1544 is logically connected to computer 1512 through a network interface 1548 and then physically connected via communication connection 1550. Network interface 1548 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1550 refer(s) to hardware/software employed to connect network interface 1548 to bus 1518. While communication connection 1550 is shown for illustrative clarity inside computer 1512, it can also be external to computer 1512. The hardware/software for connection to network interface 1548 can include, for example, internal and external technologies such as modems, including regular telephone grade modems, cable modems and DSL modems, ISDN adapters, and Ethernet cards.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

With respect to any figure or numerical range for a given characteristic, a figure or a parameter from one range may be combined with another figure or a parameter from a different range for the same characteristic to generate a numerical range.

Other than where otherwise indicated, all numbers, values and/or expressions referring to quantities of detectable materials, conditions, etc., used in the specification and claims are to be understood as modified in all instances by the term "about."

In this regard, while the disclosed subject matter is described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A telemonitoring system for improving healthcare, comprising:
    a memory to store machine instructions; and
    a processor, coupled to the memory, that executes the machine instructions to perform operations, comprising:
    receiving an ambient value of ambient values from a sensor device of a group of sensor devices relating to indoor air quality affecting healthcare, wherein the sensor device is located in a habitable structure, the sensor device comprising at least one of a particulate sensor, a temperature sensor, a relative humidity sensor, a volatile organic compounds sensor, a nitrogen oxides sensor, a carbon monoxide sensor, a combustible gas sensor, a carbon dioxide sensor, and a formaldehyde sensor;
    as a function of the ambient value, establishing a baseline threshold value for the habitable structure;
    based on the baseline threshold value, adjusting a parameter value associated with the sensor device; and
    a notification component that provides a notification to take remedial measures when the ambient value exceeds the baseline threshold value.

2. The telemonitoring system for improving healthcare of claim 1, wherein the operations further comprise, establishing the base line threshold value as a function of a historical baseline threshold value of historical baseline threshold values associated with the habitable structure.

3. The telemonitoring system for improving healthcare of claim 1, wherein the notification component uses e-mail, short message service, multimedia messaging service, or a paging service to provide the notification.

4. The telemonitoring system for improving healthcare of claim 1, wherein the operations further comprise in response to a change in the parameter value, the sensor device facilitates a change in operating state associated with a climate control device.

5. The telemonitoring system for improving healthcare of claim 1, wherein the operations further comprise, adjusting the parameter value in response to determining that a benefit associated with adjusting the parameter value is greater that a cost associated with adjusting the parameter value.

6. The telemonitoring system for improving healthcare of claim 1, wherein the ambient value is a first ambient value and the sensor device is a first sensor device, and wherein the operations further comprise, establishing the baseline threshold value as a function of a second ambient value associated with a second sensor device of the group of sensor devices.

7. The telemonitoring system for improving healthcare of claim 6, wherein the first sensor device is in wireless communication with the second sensor device.

8. The telemonitoring system for improving healthcare of claim 1, wherein the ambient value is a first ambient value and the group of sensor devices is a first group of sensor devices, and wherein the operations further comprise establishing the baseline threshold value as a function of a second ambient value associated with a second sensor device of a second group of sensor devices.

9. The telemonitoring system for improving healthcare of claim 8, wherein the sensor device is a first sensor device, and wherein the operations further comprise establishing a wireless communication via the first sensor device of the first group of sensor devices to the second sensor device of the second group of sensor devices.

10. The telemonitoring system for improving healthcare of claim 9, wherein the first sensor device is a relative humidity sensor device.

11. The telemonitoring system for improving healthcare of claim 9, wherein the second sensor device is a carbon monoxide sensor device.

12. A store and forward device for a telemedicine system, comprising:
    a processor that executes instructions to perform operations comprising:
    receiving ambient value data of a group of ambient values, wherein the ambient value data is associated with a group of sensor devices situated within a residential structure relating to indoor air quality affecting healthcare, the sensor device comprising at least one of a particulate sensor, a temperature sensor, a relative humidity sensor, a volatile organic compounds sensor, a nitrogen oxides sensor, a carbon monoxide sensor, a combustible gas sensor, a carbon dioxide sensor, and a formaldehyde sensor;
    compressing the ambient value data to form aggregation data representing an aggregation of values associated the group of sensor devices; and
    initiating transmission of the aggregation data to a server device; and
    providing a notification to take remedial measures when the ambient value exceeds the baseline threshold value.

13. The store and forward device of claim 12, wherein the operations further comprise facilitating the server device to generate, based on the aggregation data, an environmental finger print associated with a defined area within the residential structure.

14. The store and forward device of claim 13, wherein the operations further comprise facilitating the server device to return the environmental finger print data to a sensor device of the group of sensor devices.

15. The store and forward device of claim 14, wherein the operations further comprise facilitating the sensor device to change, based on the environmental finger print data, a state associated with a climate control device from a first state to a second state.

16. The store and forward device of claim 12, wherein the group of devices comprises a digital camera.

17. The store and forward device of claim 12, wherein the group of devices comprises a motion sensor device.

18. A telemedicine communication method, comprising:
receiving an ambient value of ambient values from a sensor device of a group of sensor devices relating to indoor air quality affecting healthcare, wherein the sensor device is located in a habitable structure, the sensor device comprising at least one of a particulate sensor, a temperature sensor, a relative humidity sensor, a volatile organic compounds sensor, a nitrogen oxides sensor, a carbon monoxide sensor, a combustible gas sensor, a carbon dioxide sensor, and a formaldehyde sensor;
as a function of the ambient value, establishing a baseline threshold value for the habitable structure;
based on the baseline threshold value, adjusting a parameter value associated with the sensor device; and
providing a notification to take remedial measures when the ambient value exceeds the baseline threshold value.

19. The telemedicine communication method of claim 18, further comprising: establishing the base line threshold value as a function of a historical baseline threshold value of historical baseline threshold values associated with the habitable structure.

20. The telemedicine communication monitor method of claim 18, wherein providing the notification comprises sending at least one of an e-mail, a short message, a multimedia message, or a page.

* * * * *